United States Patent
Matsuo et al.

(10) Patent No.: US 8,575,213 B2
(45) Date of Patent: Nov. 5, 2013

(54) PYRETHRINOID-TYPE ESTERS AS PESTICIDES

(75) Inventors: Noritada Matsuo, Amagasaki (JP); Tatsuya Mori, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/637,186

(22) PCT Filed: Mar. 18, 2011

(86) PCT No.: PCT/JP2011/057501
§ 371 (c)(1),
(2), (4) Date: Sep. 25, 2012

(87) PCT Pub. No.: WO2011/122507
PCT Pub. Date: Jun. 10, 2011

(65) Prior Publication Data
US 2013/0018098 A1     Jan. 17, 2013

(30) Foreign Application Priority Data
Mar. 31, 2010   (JP) .................................. 2010-081658

(51) Int. Cl.
  *A01N 37/34*   (2006.01)
  *A61K 31/275*  (2006.01)
(52) U.S. Cl.
  USPC .......................................... 514/521; 558/426
(58) Field of Classification Search
  None
  See application file for complete search history.

(56) References Cited

U.S. PATENT DOCUMENTS 4,602,038 A     7/1986   Tessier et al.

FOREIGN PATENT DOCUMENTS

JP   57-158765 A    9/1982
WO   2008001946 A2  1/2008

OTHER PUBLICATIONS

Int'l Search Report and Written Opinion issued Jun. 14, 2011 in Int'l Application No. PCT/JP2011/057501.
Int'l Preliminary Report on Patentability issued Oct. 2, 2012 in Int'l Application No. PCT/JP2011/057501.

*Primary Examiner* — Brandon Fetterolf
*Assistant Examiner* — Jean Cornet
(74) *Attorney, Agent, or Firm* — Panitch Schwarze Belisario & Nadel LLP

(57) ABSTRACT

An ester compound represented by formula (1): wherein $R^1$ represents hydrogen, fluorine, C1-C4 alkyl, C1-C4 alkoxy, C1-C4 alkoxymethyl, or C1-C4 alkylthiomethyl; $R^3$ represents hydrogen or methyl, $R^4$ represents hydrogen or C1-C4 alkyl, and $R^5$ represents hydrogen or C1-C4 alkyl; has an excellent pest control effect and is therefore useful as an active ingredient of a pest control agent.

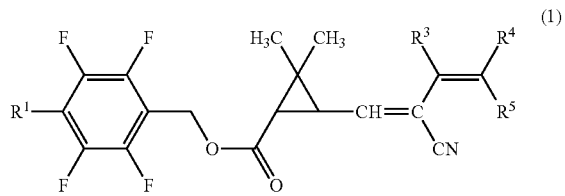

31 Claims, No Drawings

PYRETHRINOID-TYPE ESTERS AS PESTICIDES

CROSS-REFERENCE TO RELATED APPLICATION

This application is a Section 371 of International Application No. PCT/JP2011/057501, filed Mar. 18, 2011, which was published in the English language on Oct. 6, 2011, under International Publication No. WO 2011/122507 A1 the disclosure of which is incorporated herein by reference.

TECHNICAL FIELD

The present invention relates to an ester compound and use thereof.

BACKGROUND ART

Heretofore, various compounds have been synthesized so as to control pests. For example, a certain ester compound is described in JP-A-57-158765.

DISCLOSURE OF INVENTION

An object of the present invention is to provide a novel compound having an excellent pest control effect.

The present inventors have intensively studied and found that an ester compound represented by formula (1) shown below has an excellent pest control effect, and led to the present invention.

That is, the present invention is directed to the following invention:

[1] An ester compound represented by formula (1):

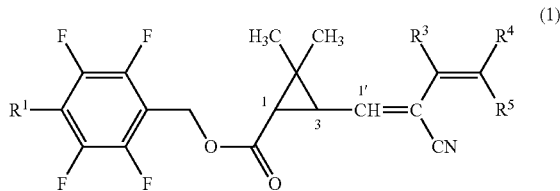

wherein $R^1$ represents hydrogen, fluorine, C1-C4 alkyl, C1-C4 alkoxy, C1-C4 alkoxymethyl, or C1-C4 alkylthiomethyl; $R^3$ represents hydrogen or methyl, $R^4$ represents hydrogen or C1-C4 alkyl, and $R^5$ represents hydrogen or C1-C4 alkyl (hereinafter referred to as the compound of the present invention);

[2] The ester compound according to [1], wherein a relative configuration of the substituent at the 1-position of the cyclopropane ring and the substituent at the 3-position of the cyclopropane ring is a trans configuration in formula (1);

[3] The ester compound according to [1], wherein an absolute configuration of the 1-position of the cyclopropane ring is an R configuration in formula (1);

[4] The ester compound according to [1], wherein an absolute configuration of the 1-position of the cyclopropane ring is an R configuration, and a relative configuration of the substituent at the 1-position of the cyclopropane ring and the substituent at the 3-position of the cyclopropane ring is a trans configuration in formula (1);

[5] The ester compound according to [1], wherein a relative configuration of the substituent of the 1'-position existing on the substituent at the 3-position of the cyclopropane ring is Z-configuration in formula (1);

[6] The ester compound according to [1], wherein an absolute configuration of the 1-position of the cyclopropane ring is an R configuration and a relative configuration of the substituent of the 1'-position existing on the substituent at the 3-position of the cyclopropane ring is Z-configuration in formula (1);

[7] The ester compound according to [1], wherein an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration in formula (1);

[8] The ester compound according to any one of [1] to [7], wherein $R^3$ is hydrogen in formula (1);

[9] The ester compound according to any one of [1] to [7]; wherein $R^4$ is hydrogen or methyl in formula (1);

[10] The ester compound according to any one of [1] to [7], wherein $R^4$ is hydrogen in formula (1);

[11] The ester compound according to any one of [1] to [7], wherein $R^4$ is methyl in formula (1);

[12] The ester compound according to any one of [1] to [7], wherein $R^5$ is hydrogen in formula (1);

[13] The ester compound according to any one of [1] to [7], wherein $R^3$ is hydrogen and $R^4$ is hydrogen or methyl in formula (1);

[14] The ester compound according to any one of [1] to [7], wherein $R^3$ is hydrogen and $R^4$ is hydrogen in formula (1);

[15] The ester compound according to any one of [1] to [7], wherein $R^3$ is hydrogen and $R^4$ is methyl in formula (1);

[16] The ester compound according to any one of [1] to [7], wherein $R^3$ is hydrogen and $R^5$ is hydrogen in formula (1);

[17] The ester compound according to any one of [1] to [7], wherein $R^4$ is hydrogen or methyl, and $R^5$ is hydrogen in formula (1);

[18] The ester compound according to any one of [1] to [7], wherein $R^4$ is hydrogen and $R^5$ is hydrogen in formula (1);

[19] The ester compound according to any one of [1] to [7], wherein $R^4$ is methyl and $R^5$ is hydrogen in formula (1);

[20] The ester compound according to any one of [1] to [7], wherein $R^3$ is hydrogen, $R^4$ is hydrogen or methyl, and $R^5$ is hydrogen in formula (1);

[21] The ester compound according to any one of [1] to [7], wherein $R^3$ is hydrogen, $R^4$ is hydrogen, and $R^5$ is hydrogen in formula (1);

[22] The ester compound according to any one of [1] to [7], wherein $R^3$ is hydrogen, $R^4$ is methyl, and $R^5$ is hydrogen in formula (1);

[23] The ester compound according to any one of [1] to [22], wherein $R^1$ is methoxymethyl in formula (1);

[24] A pest control agent comprising the ester compound according to any one of [1] to [23] and an inert carrier;

[25] A method of controlling pests, which comprises a step of applying an effective amount of the ester compound according to any one of [1] to [23] to pests or a place where pests habitat;

[26] A method of controlling pests, which comprises the step of applying an effective amount of the ester compound according to any one of [1] to [23] to cockroaches or a place where cockroaches inhabits;

[27] The method of controlling pests according to [26], wherein the cockroach is American cockroach (*Periplaneta Americana*);

[28] The method of controlling pests according to [26], wherein the cockroach is German cockroach (*Blattella germanica*);

[29] A method of controlling pests, which comprises a step of spraying an effective amount of the ester compound according to any one of [1] to [23] to cockroaches or a place where cockroaches inhabit;

[30] The method of controlling pests according to [29], wherein the cockroach is American cockroach (*Periplaneta Americana*);

[31] The method of controlling pests according to [29], wherein the cockroach is German cockroach (*Blattella germanica*).

The compound of the present invention has an excellent pest control effect and is therefore useful as an active ingredient of a pest control agent.

In the compound of the present invention, there are isomers derived from two asymmetric carbon atoms at the 1-position and the 3-position on the cyclopropane ring, and isomers derived from the double bond present in the substituent at the 3-position of the cyclopropane ring. Each isomer having pest control activity or a mixture of those isomers in an arbitrary ratio which has pest control activity are included in the present invention.

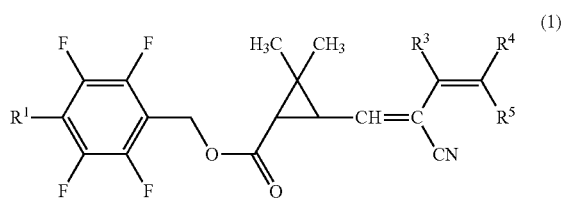

Examples of C1-C4 alkyl represented by $R^1$ include methyl. Examples of C1-C4 alkoxy represented by $R^1$ include methoxy. Examples of C1-C4 alkoxymethyl represented by $R^1$ include methoxymethyl. Examples of C1-C4 alkylthiomethyl represented by $R^1$ include methylthiomethyl.

Examples of the C1-C4 alkyl represented by $R^4$ include methyl, ethyl, propyl, butyl and isopropyl, and the C1-C4 alkyl represented by $R^5$ include methyl, ethyl, propyl, butyl and isopropyl.

Examples of the compound of the present invention include the following compounds.

An ester compound represented by formula (1) in which a relative configuration of the substituent at the 1-position of the cyclopropane ring and the substituent at the 3-position of the cyclopropane ring is a trans configuration.

An ester compound represented by formula (1) in which an absolute configuration of the 1-position of the cyclopropane ring is an R configuration.

An ester compound represented by formula (1) in which an absolute configuration of the 1-position of the cyclopropane ring is an R configuration, and a relative configuration of the substituent at the 1-position of the cyclopropane ring and the substituent at the 3-position of the cyclopropane ring is a trans configuration.

An ester compound represented by formula (1) in which a relative configuration of the substituent of the 1'-position existing on the substituent at the 3-position of the cyclopropane ring is Z-configuration.

An ester compound represented by formula (1) in which an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^3$ is hydrogen.

An ester compound represented by formula (1) in which a relative configuration of the substituent at the 1-position of the cyclopropane ring and the substituent at the 3-position of the cyclopropane ring is a trans configuration, and $R^3$ is hydrogen.

An ester compound represented by formula (1) in which an absolute configuration of the 1-position of the cyclopropane ring is an R configuration, and $R^3$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, and $R^3$ is hydrogen.

An ester compound represented by formula (1) in which $R^3$ is hydrogen and a relative configuration of the substituent of the 1'-position existing on the substituent at the 3-position of the cyclopropane ring is Z-configuration.

An ester compound represented by formula (1) in which $R^3$ is hydrogen and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^3$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^4$ is hydrogen or methyl.

An ester compound represented by formula (1) in which a relative configuration of the substituent at the 1-position of the cyclopropane ring and the substituent at the 3-position of the cyclopropane ring is a trans configuration, and $R^4$ is hydrogen or methyl.

An ester compound represented by formula (1) in which an absolute configuration of the 1-position of the cyclopropane ring is an R configuration, and $R^4$ is hydrogen or methyl.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, and $R^4$ is hydrogen or methyl.

An ester compound represented by formula (1) in which $R^4$ is hydrogen or methyl, and a relative configuration of the substituent of the 1'-position existing on the substituent at the 3-position of the cyclopropane ring is Z-configuration.

An ester compound represented by formula (1) in which $R^4$ is hydrogen or methyl, and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^4$ is hydrogen or methyl, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^4$ is hydrogen.

An ester compound represented by formula (1) in which a relative configuration of the substituent at the 1-position of the cyclopropane ring and the substituent at the 3-position of the cyclopropane ring is a trans configuration, and $R^4$ is hydrogen.

An ester compound represented by formula (1) in which an absolute configuration of the 1-position of the cyclopropane ring is an R configuration, and $R^4$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, and $R^4$ is hydrogen.

An ester compound represented by formula (1) in which $R^4$ is hydrogen and a relative configuration of the substituent of the 1'-position existing on the substituent at the 3-position of the cyclopropane ring is Z-configuration.

An ester compound represented by formula (1) in which $R^4$ is hydrogen and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^4$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^4$ is methyl.

An ester compound represented by formula (1) in which a relative configuration of the substituent at the 1-position of the cyclopropane ring and the substituent at the 3-position of the cyclopropane ring is a trans configuration, and $R^4$ is methyl.

An ester compound represented by formula (1) in which an absolute configuration of the 1-position of the cyclopropane ring is an R configuration, and $R^4$ is methyl.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, and $R^4$ is methyl.

An ester compound represented by formula (1) in which $R^4$ is methyl and a relative configuration of the substituent of the 1'-position existing on the substituent at the 3-position of the cyclopropane ring is Z-configuration.

An ester compound represented by formula (1) in which $R^4$ is methyl and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^4$ is methyl, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^5$ is hydrogen.

An ester compound represented by formula (1) in which a relative configuration of the substituent at the 1-position of the cyclopropane ring and the substituent at the 3-position of the cyclopropane ring is a trans configuration, and $R^5$ is hydrogen.

An ester compound represented by formula (1) in which an absolute configuration of the 1-position of the cyclopropane ring is an R configuration, and $R^5$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, and $R^5$ is hydrogen.

An ester compound represented by formula (1) in which $R^5$ is hydrogen and a relative configuration of the substituent of the 1'-position existing on the substituent at the 3-position of the cyclopropane ring is Z-configuration.

An ester compound represented by formula (1) in which $R^5$ is hydrogen and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^5$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^3$ is hydrogen and $R^4$ is hydrogen or methyl.

An ester compound represented by formula (1) in which a relative configuration of the substituent at the 1-position of the cyclopropane ring and the substituent at the 3-position of the cyclopropane ring is a trans configuration, $R^3$ is hydrogen and $R^4$ is hydrogen or methyl.

An ester compound represented by formula (1) in which an absolute configuration of the 1-position of the cyclopropane ring is an R configuration, and $R^3$ is hydrogen and $R^4$ is hydrogen or methyl.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^3$ is hydrogen and $R^4$ is hydrogen or methyl.

An ester compound represented by formula (1) in which $R^3$ is hydrogen and $R^4$ is hydrogen or methyl, and a relative configuration of the substituent of the 1'-position existing on the substituent at the 3-position of the cyclopropane ring is Z-configuration.

An ester compound represented by formula (1) in which $R^3$ is hydrogen, $R^4$ is hydrogen or methyl, and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) In which $R^3$ is hydrogen, $R^4$ is hydrogen or methyl, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^3$ is hydrogen and $R^4$ is hydrogen.

An ester compound represented by formula (1) in which a relative configuration of the substituent at the 1-position of the cyclopropane ring and the substituent at the 3-position of the cyclopropane ring is a trans configuration, $R^3$ is hydrogen and $R^4$ is hydrogen.

An ester compound represented by formula (1) in which an absolute configuration of the 1-position of the cyclopropane ring is an R configuration, and $R^3$ is hydrogen and $R^4$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^3$ is hydrogen and $R^4$ is hydrogen.

An ester compound represented by formula (1) in which $R^3$ is hydrogen, $R^4$ is hydrogen, and a relative configuration of the substituent of the 1'-position existing on the substituent at the 3-position of the cyclopropane ring is Z-configuration.

An ester compound represented by formula (1) in which $R^3$ is hydrogen, $R^4$ is hydrogen, and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^3$ is hydrogen, $R^4$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^3$ is hydrogen and $R^4$ is methyl.

An ester compound represented by formula (1) in which a relative configuration of the substituent at the 1-position of the cyclopropane ring and the substituent at the 3-position of the cyclopropane ring is a trans configuration, $R^3$ is hydrogen and $R^4$ is methyl.

An ester compound represented by formula (1) in which an absolute configuration of the 1-position of the cyclopropane ring is an R configuration, $R^3$ is hydrogen and $R^4$ is methyl.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^3$ is hydrogen and $R^4$ is methyl.

An ester compound represented by formula (1) in which $R^3$ is hydrogen, $R^4$— is methyl and a relative configuration of the substituent of the 1'-position existing on the substituent at the 3-position of the cyclopropane ring is Z-configuration.

An ester compound represented by formula (1) in which $R^3$ is hydrogen, $R^4$ is methyl, and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^3$ is hydrogen, $R^4$ is methyl, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^3$ is hydrogen and $R^5$ is hydrogen.

An ester compound represented by formula (1) in which a relative configuration of the substituent at the 1-position of the cyclopropane ring and the substituent at the 3-position of the cyclopropane ring is a trans configuration, $R^3$ is hydrogen and $R^5$ is hydrogen.

An ester compound represented by formula (1) in which an absolute configuration of the 1-position of the cyclopropane ring is an R configuration, $R^3$ is hydrogen and $R^5$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^3$ is hydrogen and $R^5$ is hydrogen.

An ester compound represented by formula (1) in which $R^3$ is hydrogen, $R^5$ is hydrogen and a relative configuration of the substituent of the 1'-position existing on the substituent at the 3-position of the cyclopropane ring is Z-configuration.

An ester compound represented by formula (1) in which $R^3$ is hydrogen, $R^5$ is hydrogen, and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^3$ is hydrogen, $R^5$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^4$ is hydrogen or methyl, and $R^5$ is hydrogen.

An ester compound represented by formula (1) in which a relative configuration of the substituent at the 1-position of the cyclopropane ring and the substituent at the 3-position of the cyclopropane ring is a trans configuration, $R^4$ is hydrogen or methyl, and $R^5$ is hydrogen.

An ester compound represented by formula (1) in which an absolute configuration of the 1-position of the cyclopropane ring is an R configuration, $R^4$ is hydrogen or methyl, and $R^5$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^4$ is hydrogen or methyl, and $R^5$ is hydrogen.

An ester compound represented by formula (1) in which $R^4$ is hydrogen or methyl, $R^5$ is hydrogen, and a relative configuration of the substituent of the 1'-position existing on the substituent at the 3-position of the cyclopropane ring is Z-configuration.

An ester compound represented by formula (1) in which $R^4$ is hydrogen or methyl, $R^5$ is hydrogen, and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^4$ is hydrogen or methyl, $R^5$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^4$ is hydrogen and $R^5$ is hydrogen.

An ester compound represented by formula (1) in which a' relative configuration of the substituent at the 1-position of the cyclopropane ring and the substituent at the 3-position of the cyclopropane ring is a trans configuration, $R^4$ is hydrogen and $R^5$ is hydrogen.

An ester compound represented by formula (1) in which an absolute configuration of the 1-position of the cyclopropane ring is an R configuration, $R^4$ is hydrogen and $R^5$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^4$ is hydrogen and $R^5$ is hydrogen.

An ester compound represented by formula (1) in which $R^4$ is hydrogen, $R^5$ is hydrogen, and a relative configuration of the substituent of the 1'-position existing on the substituent at the 3-position of the cyclopropane ring is Z-configuration.

An ester compound represented by formula (1) in which $R^4$ is hydrogen, $R^5$ is hydrogen and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^4$ is hydrogen, $R^5$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^4$ is methyl and $R^5$ is hydrogen.

An ester compound represented by formula (1) in which a relative configuration of the substituent at the 1-position of the cyclopropane ring and the substituent at the 3-position of the cyclopropane ring is a trans configuration, $R^4$ is methyl and $R^5$ is hydrogen.

An ester compound represented by formula (1) in which an absolute configuration of the 1-position of the cyclopropane ring is an R configuration, $R^4$ is methyl and $R^5$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^4$ is methyl and $R^5$ is hydrogen.

An ester compound represented by formula (1) in which $R^4$ is methyl, $R^5$ is hydrogen, and a relative configuration of the substituent of the 1'-position existing on the substituent at the 3-position of the cyclopropane ring is Z-configuration.

An ester compound represented by formula (1) in which $R^4$ is methyl, $R^5$ is hydrogen and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^4$ is methyl, $R^5$ is hydrogen, an absolute configuration of the 1-position of the cyclopropane ring is an R configuration, a relative configuration of the substituent at the 1-position of the cyclopropane ring and the substituent at the 3-position of the cyclopropane ring, is a trans configuration, and a relative configuration of the substituent of the 1'-position existing on the substituent at the 3-position of the cyclopropane ring is Z-configuration.

An ester compound represented by formula (1) in which $R^3$ is hydrogen, $R^4$ is hydrogen or methyl, and $R^5$ is hydrogen.

An ester compound represented by formula (1) in which a relative configuration of the substituent at the 1-position of the cyclopropane ring and the substituent at the 3-position of the cyclopropane ring is a trans configuration, $R^3$ is hydrogen, $R^4$ is hydrogen or methyl, and $R^5$ is hydrogen.

An ester compound represented by formula (1) in which an absolute configuration of the 1-position of the cyclopropane ring is an R configuration, $R^3$ is hydrogen, $R^4$ is hydrogen or methyl, and $R^5$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^3$ is hydrogen, $R^4$ is hydrogen or methyl, and $R^5$ is hydrogen.

An ester compound represented by formula (1) in which $R^3$ is hydrogen, $R^4$ is hydrogen or methyl, $R^5$ is hydrogen, and a relative configuration of the substituent of the 1'-position existing on the substituent at the 3-position of the cyclopropane ring is Z-configuration.

An ester compound represented by formula (1) in which $R^3$ is hydrogen, $R^4$ is hydrogen or methyl, $R^5$ is hydrogen, and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^3$ is hydrogen, $R^4$ is hydrogen or methyl, $R^5$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^3$ is hydrogen, $R^4$ is hydrogen, and $R^5$ is hydrogen.

An ester compound represented by formula (1) in which a relative configuration of the substituent at the 1-position of the cyclopropane ring and the substituent at the 3-position of the cyclopropane ring is a trans configuration, $R^3$ is hydrogen, $R^4$ is hydrogen, and $R^5$ is hydrogen.

An ester compound represented by formula (1) in which an absolute configuration of the 1-position of the cyclopropane ring is an R configuration, $R^3$ is hydrogen, $R^4$ is hydrogen, and $R^5$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^3$ is hydrogen, $R^4$ is hydrogen, and $R^5$ is hydrogen.

An ester compound represented by formula (1) in which $R^3$ is hydrogen, $R^4$ is hydrogen, $R^5$ is hydrogen, and a relative configuration of the substituent of the 1'-position existing on the substituent at the 3-position of the cyclopropane ring is Z-configuration.

An ester compound represented by formula (1) in which $R^3$ is hydrogen, $R^4$ is hydrogen, $R^5$ is hydrogen, and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^3$ is hydrogen, $R^4$ is hydrogen, $R^5$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^3$ is hydrogen, $R^4$ is methyl, and $R^5$ is hydrogen.

An ester compound represented by formula (1) in which a relative configuration of the substituent at the 1-position of the cyclopropane ring and the substituent at the 3-position of the cyclopropane ring is a trans configuration, $R^3$ is hydrogen, $R^4$ is methyl, and $R^5$ is hydrogen.

An ester compound represented by formula (1) in which an absolute configuration of the 1-position of the cyclopropane ring is an R configuration, $R^3$ is hydrogen, $R^4$ is methyl, and $R^5$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^3$ is hydrogen, $R^4$ is methyl, and $R^5$ is hydrogen.

An ester compound represented by formula (1) in which $R^3$ is hydrogen, $R^4$ is methyl, $R^5$ is hydrogen, and a relative configuration of the substituent of the 1'-position existing on the substituent at the 3-position of the cyclopropane ring is Z-configuration.

An ester compound represented by formula (1) in which $R^3$ is hydrogen, $R^4$ is methyl, $R^5$ is hydrogen, and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^3$ is hydrogen, $R^4$ is methyl, $R^5$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which a relative configuration of the substituent at the 1-position of the cyclopropane ring and the substituent at the 3-position of the cyclopropane ring is a trans configuration and $R^1$ is methoxymethyl.

An ester compound represented by formula (1) in which an absolute configuration of the 1-position of the cyclopropane ring is an R configuration and $R^1$ is methoxymethyl.

An ester compound represented by formula (1) in which an absolute configuration of the 1-position of the cyclopropane ring is an R configuration, and a relative configuration of the substituent at the 1-position of the cyclopropane ring and the substituent at the 3-position of the cyclopropane ring is a trans configuration and $R^1$ is methoxymethyl.

An ester compound represented by formula (1) in which a relative configuration of the substituent of the 1'-position existing on the substituent at the 3-position of the cyclopropane ring is Z-configuration and $R^1$ is methoxymethyl.

An ester compound represented by formula (1) in which an absolute configuration of the 1-position of the cyclopropane ring is an R configuration, a relative configuration of the substituent of the 1'-position existing on the substituent at the 3-position of the cyclopropane ring is Z-configuration and $R^1$ is methoxymethyl.

An ester compound represented by formula (1) in which an absolute configuration of the 1-position of the cyclopropane ring is an R configuration, a relative configuration of the substituent at the 1-position of the cyclopropane ring, the substituent at the 3-position of the cyclopropane ring is a trans configuration, and a relative configuration of the substituent of the 1'-position existing on the substituent at the 3-position of the cyclopropane ring is Z-configuration and $R^1$ is methoxymethyl.

An ester compound represented by formula (1) in which $R^1$ is methoxymethyl and $R^3$ is hydrogen.

An ester compound represented by formula (1) in which a relative configuration of the substituent at the 1-position of the cyclopropane ring and the substituent at the 3-position of the cyclopropane ring is a trans configuration, $R^1$ is methoxymethyl and $R^3$ is hydrogen.

An ester compound represented by formula (1) in which an absolute configuration of the 1-position of the cyclopropane ring is an R configuration, $R^1$ is methoxymethyl and $R^3$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^1$ is methoxymethyl and $R^3$ is hydrogen.

An ester compound represented by formula (1) in which $R^1$ is methoxymethyl, $R^3$ is hydrogen and a relative configuration of the substituent of the 1'-position existing on the substituent at the 3-position of the cyclopropane ring is Z-configuration.

An ester compound represented by formula (1) in which. $R^1$ is methoxymethyl, $R^3$ is hydrogen and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^1$ is methoxymethyl, and $R^4$ is hydrogen or methyl.

An ester compound represented by formula (1) in which a relative configuration of the substituent at the 1-position of the cyclopropane ring and the substituent at the 3-position of the cyclopropane ring is a trans configuration, $R^1$ is methoxymethyl, and $R^4$ is hydrogen or methyl.

An ester compound represented by formula (1) in which an absolute configuration of the 1-position of the cyclopropane ring is an R configuration, $R^1$ is methoxymethyl, and $R^4$ is hydrogen or methyl.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^1$ is methoxymethyl, and $R^4$ is hydrogen or methyl.

An ester compound represented by formula (1) in which $R^1$ is methoxymethyl, $R^4$ is hydrogen or methyl, and a relative configuration of the substituent of the 1'-position existing on the substituent at the 3-position of the cyclopropane ring is Z-configuration.

An ester compound represented by formula (1) in which $R^1$ is methoxymethyl, $R^4$ is hydrogen or methyl, and an absolute configuration of the 1-position of the cyclopropane ring is an R configuration and a"relative configuration of the substituent of the 1'-position existing on the substituent at the 3-position of the cyclopropane ring is Z-configuration.

An ester compound represented by formula (1) in which $R^1$ is methoxymethyl, $R^4$ is hydrogen or methyl, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^1$ is methoxymethyl and $R^4$ is hydrogen.

An ester compound represented by formula (1) in which a relative configuration of the substituent at the 1-position of the cyclopropane ring and the substituent at the 3-position of the cyclopropane ring is a trans configuration, $R^1$ is methoxymethyl, and $R^4$ is hydrogen.

An ester compound represented by formula (1) in which an absolute configuration of the 1-position of the cyclopropane ring is an R configuration, $R^1$ is methoxymethyl, and $R^4$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^1$ is methoxymethyl, and $R^4$ is hydrogen.

An ester compound represented by formula (1) in which $R^1$ is methoxymethyl, $R^4$ is hydrogen and a relative configuration of the substituent of the 1'-position existing on the substituent at the 3-position of the cyclopropane ring is Z-configuration.

An ester compound represented by formula (1) in which $R^1$ is methoxymethyl, $R^4$ is hydrogen and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^1$ is methoxymethyl, $R^4$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^1$ is methoxymethyl and $R^4$ is methyl.

An ester compound represented by formula (1) in which a relative configuration of the substituent at the 1-position of the cyclopropane ring and the substituent at the 3-position of the cyclopropane ring is a trans configuration, $R^1$ is methoxymethyl, and $R^4$ is methyl.

An ester compound represented by formula (1) in which an absolute configuration of the 1-position of the cyclopropane ring is an R configuration, $R^1$ is methoxymethyl, and $R^4$ is methyl.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^1$ is methoxymethyl, and $R^4$ is methyl.

An ester compound represented by formula (1) in which $R^1$ is methoxymethyl, $R^4$ is methyl and a relative configuration of the substituent of the 1'-position existing on the substituent at the 3-position of the cyclopropane ring is Z-configuration.

An ester compound represented by formula (1) in which $R^1$ is methoxymethyl, $R^4$ is methyl and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^1$ is methoxymethyl, $R^4$ is methyl, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^1$ is methoxymethyl and $R^5$ is hydrogen.

An ester compound represented by formula (1) in which a relative configuration of the substituent at the 1-position of the cyclopropane ring and the substituent at the 3-position of the cyclopropane ring is a trans configuration, $R^1$ is methoxymethyl, and $R^5$ is hydrogen.

An ester compound represented by formula (1) in which an absolute configuration of the 1-position of the cyclopropane ring is an R configuration, $R^1$ is methoxymethyl, and $R^5$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^1$ is methoxymethyl, and $R^5$ is hydrogen.

An ester compound represented by formula (1) in which $R^1$ is methoxymethyl, $R^5$ is hydrogen and a relative configuration of the substituent of the 1'-position existing on the substituent at the 3-position of the cyclopropane ring is Z-configuration.

An ester compound represented by formula (1) in which $R^1$ is methoxymethyl, $R^5$ is hydrogen and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^1$ is methoxymethyl, $R^5$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen and $R^4$ is hydrogen or methyl.

An ester compound represented by formula (1) in which a relative configuration of the substituent at the 1-position of the cyclopropane ring and the substituent at the 3-position of the cyclopropane ring is a trans configuration, $R^1$ is methoxymethyl, $R^3$ is hydrogen and $R^4$ is hydrogen or methyl.

An ester compound represented by formula (1) in which an absolute configuration of the 1-position of the cyclopropane ring is an R configuration, $R^1$ is methoxymethyl, $R^3$ is hydrogen and $R^4$ is hydrogen or methyl.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^1$ is methoxymethyl, $R^3$ is hydrogen and $R^4$ is hydrogen or methyl.

An ester compound represented by formula (1) in which $R^1$ is methoxymethyl, $R^3$ is hydrogen and $R^4$ is hydrogen or methyl, and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen, $R^4$ is hydrogen or methyl, and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen, $R^4$ is hydrogen or methyl, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen and $R^4$ is hydrogen.

An ester compound represented by formula (1) in which a relative configuration of the substituent at the 1-position of the cyclopropane ring and the substituent at the 3-position of the cyclopropane ring is a trans configuration, $R^1$ is methoxymethyl, $R^3$ is hydrogen and $R^4$ is hydrogen.

An ester compound represented by formula (1) in which an absolute configuration of the 1-position of the cyclopropane ring is an R configuration, $R^1$ is methoxymethyl, $R^3$ is hydrogen and $R^4$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^1$ is methoxymethyl, $R^3$ is hydrogen and $R^4$ is hydrogen.

An ester compound represented by formula (1) in which $R^1$ is methoxymethyl, $R^3$ is hydrogen, $R^4$ is hydrogen, and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen, $R^4$ is hydrogen, and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen, $R^4$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen and $R^4$ is methyl.

An ester compound represented by formula (1) in which a relative configuration of the substituent at the 1-position of the cyclopropane ring and the substituent at the 3-position of the cyclopropane ring is a trans configuration, $R^1$ is methoxymethyl, $R^3$ is hydrogen and $R^4$ is methyl.

An ester compound represented by formula (1) in which an absolute configuration of the 1-position of the cyclopropane ring is an R configuration, $R^1$ is methoxymethyl, $R^3$ is hydrogen and $R^4$ is methyl.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^1$ is methoxymethyl, $R^3$ is hydrogen and $R^4$ is methyl.

An ester compound represented by formula (1) in which $R^1$ is methoxymethyl, $R^3$ is hydrogen, $R^4$ is methyl and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen, $R^4$ is methyl, and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen, $R^4$ is methyl, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen and $R^5$ is hydrogen.

An ester compound represented by formula (1) in which a relative configuration of the substituent at the 1-position of the cyclopropane ring and the substituent at the 3-position of the cyclopropane ring is a trans configuration, $R^1$ is methoxymethyl, $R^3$ is hydrogen and $R^5$ is hydrogen.

An ester compound represented by formula (1) in which an absolute configuration of the 1-position of the cyclopropane ring is an R configuration, $R^1$ is methoxymethyl, $R^3$ is hydrogen and $R^5$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^1$ is methoxymethyl, $R^3$ is hydrogen and $R^5$ is hydrogen.

An ester compound represented by formula (1) in which $R^1$ is methoxymethyl, $R^3$ is hydrogen, $R^5$ is hydrogen and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen, $R^5$ is hydrogen, and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen, $R^5$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^1$ is methoxymethyl, $R^4$ is hydrogen or methyl, and $R^5$ is hydrogen. An ester compound represented by formula (1) in which a relative configuration of the substituent at the 1-position of the cyclopropane ring and the substituent at the 3-position of the cyclopropane ring is a trans configuration, $R^1$ is methoxymethyl, $R^4$ is hydrogen or methyl, and $R^5$ is hydrogen.

An ester compound represented by formula (1) in which an absolute configuration of the 1-position of the cyclopropane ring is an R configuration, $R^1$ is methoxymethyl, $R^4$ is hydrogen or methyl, and $R^5$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^1$ is methoxymethyl, $R^4$ is hydrogen or methyl, and $R^5$ is hydrogen.

An ester compound represented by formula (1) in which $R^1$ is methoxymethyl, $R^9$ is hydrogen or methyl, $R^5$ is hydrogen, and a relative configuration of the substituent of the 1'-position existing on the substituent at the 3-position of the cyclopropane ring is Z-configuration.

An ester compound represented by formula (1) in which $R^1$ is methoxymethyl, $R^4$ is hydrogen or methyl, $R^5$ is hydrogen, and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^1$ is methoxymethyl, $R^4$ is hydrogen or methyl, $R^5$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^1$ is methoxymethyl, $R^4$ is hydrogen and $R^5$ is hydrogen.

An ester compound represented by formula (1) in which a relative configuration of the substituent at the 1-position of the cyclopropane ring and the substituent at the 3-position of the cyclopropane ring is a trans configuration, $R^1$ is methoxymethyl, $R^4$ is hydrogen and $R^5$ is hydrogen.

An ester compound represented by formula (1) in which an absolute configuration of the 1-position of the cyclopropane ring is an R configuration, $R^1$ is methoxymethyl, $R^4$ is hydrogen and $R^5$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^1$ is methoxymethyl, $R^4$ is hydrogen and $R^5$ is hydrogen.

An ester compound represented by formula (1) in which $R^1$ is methoxymethyl, $R^4$ is hydrogen, $R^5$ is hydrogen, and a relative configuration of the substituent of the 1'-position existing on the substituent at the 3-position of the cyclopropane ring is Z-configuration.

An ester compound represented by formula (1) in which $R^1$ is methoxymethyl, $R^4$ is hydrogen, $R^5$ is hydrogen and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^1$ is methoxymethyl, $R^4$ is hydrogen, $R^5$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^1$ is methoxymethyl, $R^4$ is methyl and $R^5$ is hydrogen.

An ester compound represented by formula (1) in which a relative configuration of the substituent at the 1-position of the cyclopropane ring and the substituent at the 3-position of the cyclopropane ring is a trans configuration, $R^1$ is methoxymethyl, $R^4$ is methyl and $R^5$ is hydrogen.

An ester compound represented by formula (1) in which an absolute configuration of the 1-position of the cyclopropane ring is an R configuration, $R^1$ is methoxymethyl, $R^4$ is methyl and $R^5$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^1$ is methoxymethyl, $R^4$ is methyl and $R^5$ is hydrogen.

An ester compound represented by formula (1) in which $R^1$ is methoxymethyl, $R^4$ is methyl, $R^5$ is hydrogen, and a relative configuration of the substituent of the 1'-position existing on the substituent at the 3-position of the cyclopropane ring is Z-configuration.

An ester compound represented by formula (1) in which $R^1$ is methoxymethyl, $R^4$ is methyl, $R^5$ is hydrogen and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^1$ is methoxymethyl, $R^4$ is methyl, $R^5$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen, $R^4$ is hydrogen or methyl, and $R^5$ is hydrogen.

An ester compound represented by formula (1) in which a relative configuration of the substituent at the 1-position of the cyclopropane ring and the substituent at the 3-position of the cyclopropane ring is a trans configuration, $R^1$ is methoxymethyl, $R^3$ is hydrogen, $R^4$ is hydrogen or methyl, and $R^5$ is hydrogen.

An ester compound represented by formula (1) in which an absolute configuration of the 1-position of the cyclopropane ring is an R configuration, $R^1$ is methoxymethyl, $R^3$ is hydrogen, $R^4$ is hydrogen or methyl, and $R^5$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^1$ is methoxymethyl, $R^3$ is hydrogen, $R^4$ is hydrogen or methyl, and $R^5$ is hydrogen.

An ester compound represented by formula (1) in which $R^1$ is methoxymethyl, $R^3$ is hydrogen, $R^4$ is hydrogen or methyl, $R^5$ is hydrogen, and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen, $R^4$ is hydrogen or methyl, $R^5$ is hydrogen, and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen, $R^4$ is hydrogen or methyl, $R^5$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen, $R^4$ is hydrogen, and $R^5$ is hydrogen.

An ester compound represented by formula (1) in which a relative configuration of the substituent at the 1-position of the cyclopropane ring and the substituent at the 3-position of the cyclopropane ring is a trans configuration, $R^1$ is methoxymethyl, $R^3$ is hydrogen, $R^4$ is hydrogen, and $R^5$ is hydrogen.

An ester compound represented by formula (1) in which an absolute configuration of the 1-position of the cyclopropane ring is an R configuration, $R^1$ is methoxymethyl, $R^3$ is hydrogen, $R^4$ is hydrogen, and $R^5$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^1$ is methoxymethyl, $R^3$ is hydrogen, $R^4$ is hydrogen, and $R^5$ is hydrogen.

An ester compound represented by formula (1) in which $R^1$ is methoxymethyl, $R^3$ is hydrogen, $R^4$ is hydrogen, $R^5$ is hydrogen, and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen, $R^4$ is hydrogen, $R^5$ is hydrogen, and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen, $R^4$ is hydrogen, $R^5$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen, $R^4$ is methyl, and $R^5$ is hydrogen.

An ester compound represented by formula (1) in which a relative configuration of the substituent at the 1-position of the cyclopropane ring and the substituent at the 3-position of the cyclopropane ring is a trans configuration, $R^1$ is methoxymethyl, $R^3$ is hydrogen, $R^4$ is methyl, and $R^5$ is hydrogen.

An ester compound represented by formula (1) in which an absolute configuration of the 1-position of the cyclopropane ring is an R configuration, $R^1$ is methoxymethyl, $R^3$ is hydrogen, $R^4$ is methyl, and $R^5$ is hydrogen.

An ester compound represented by formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, $R^1$ is methoxymethyl, $R^3$ is hydrogen, $R^4$ is methyl, and $R^5$ is hydrogen.

An ester compound represented by formula (1) in which $R^1$ is methoxymethyl, $R^3$ is hydrogen, $R^4$ is methyl, $R^5$ is hydrogen, and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen, $R^4$ is methyl, $R^5$ is hydrogen, and an absolute configuration of the 1-position of the cyclopropane ring is an R configuration and a relative configuration of the substituent of the 1'-position existing on the substituent at the 3-position of the cyclopropane ring is Z-configuration.

An ester compound represented by formula (1) in which $R^1$ is methoxymethyl, $R^3$ is hydrogen, $R^4$ is methyl, $R^5$ is hydrogen, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the substituent of the 1'-position existing on the substituent at the 3-position of the cyclopropane ring is Z-configuration.

The process for producing the compound of the present invention will be described below.

The compound of the present invention can be produced, for example, by the production process described below.

A process of reacting an alcohol compound represented by the formula (2):

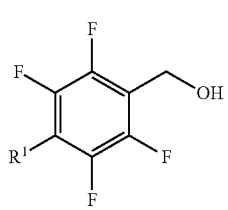

(wherein $R^1$ has the same meanings as defined above), with a carboxylic acid compound represented by the formula (3):

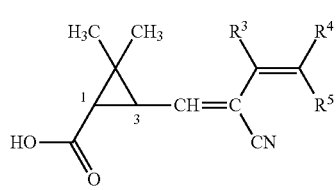

(wherein $R^3$, $R^4$ and $R^5$ have the same meanings as defined above),
or a reactive derivative thereof.

Examples of the reactive derivative include an acid halide of the carboxylic acid compound represented by the formula (3), an acid anhydride of the carboxylic acid compound, and methyl and ethyl esters of the carboxylic acid compound. Examples of the acid halide include an acid chloride compound.

The reaction is usually, carried out in the presence of a condensing agent or a base in a solvent.

Examples of the condensing agent include dicyclohexylcarbodiimide and 1-ethyl-3-(3-dimethylaminopropyl)carbodiimide hydrochloride.

Examples of the base include organic bases such as triethylamine, pyridine, N,N-diethylaniline, 4-dimethylaminopyridine and diisopropylethylamine.

Examples of the solvent include hydrocarbons such as benzene, toluene and hexane; ethers such as diethylether and tetrahydrofuran; halogenated hydrocarbons such as chloroform, dichloromethane, 1,2-dichloroethane and chlorobenzene; and a mixed solvent thereof.

The reaction time is usually within a range from 5 minutes to 72 hours.

The reaction, temperature is usually within a range from $-20°$ C. to $100°$ C. (from $-20°$ C. to a boiling point of the solvent in a case a boiling point of the solvent used is lower than $100°$ C.), and preferably $-5°$ C. to $100°$ C. (from $-5°$ C.' to a boiling point of the solvent in a case a boiling point of the solvent used is lower than $100°$ C.)

In the reaction, a use molar ratio of the alcohol compound represented by the formula (2) to the carboxylic acid compound represented by the formula (3) or the reactive derivative thereof can be optionally set, but is preferably an equimolar or near equimolar ratio.

The condensing agent or base can be usually used in any amount within a range from 0.25 mol to an excess amount, and preferably from 0.5 mol to 2 mol, based on 1 mol of the alcohol compound represented by the formula (2). These condensing agents or bases are appropriately selected according to the kind of the carboxylic acid compound represented by the formula (3) or the reactive derivative thereof.

After completion of the reaction, the reaction mixture is usually subjected to a post-treatment operation of filtering the reaction mixture and concentrating the filtrate, or pouring water into the reaction mixture, followed by extraction with an organic solvent and further concentration, and thus the compound of the present invention can be obtained. The obtained compound of the present invention can be purified by operations such as chromatography and distillation.

The alcohol compound represented by the formula (2) is a compound described in JP-A-2000-63329 or JP-A-2001-213848.

The intermediate of the present invention can be produced, for example, by the following process.

Among the carboxylic acid compound represented by the formula (3), the carboxylic acid compound represented by the formula (3-1) in which relative configuration of the substituent at the 1-position of the cyclopropane ring and the substituent at the 3-position of the cyclopropane ring is trans configuration can be produced, for example, by the following process.

That is, a carboxylic acid compound represented by the formula (3-1):

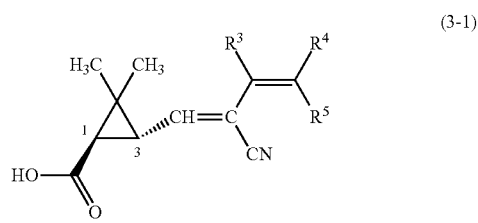

(wherein $R^3$, $R^4$ and $R^5$ have the same meanings as defined above), can be produced by reacting a caronaldehyde ester derivative represented by the formula (4-1):

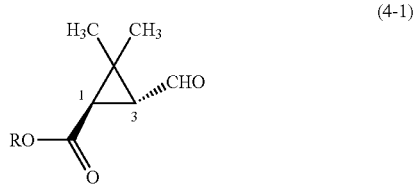

(4-1)

(wherein R represents a C1-C4 alkyl group), with a nitrile compound represented by the formula (5):

(5)

(wherein $R^3$, $R^4$ and $R^5$ have the same meanings as defined above), in the presence of a base to obtain the compound represented by the formula (6-1):

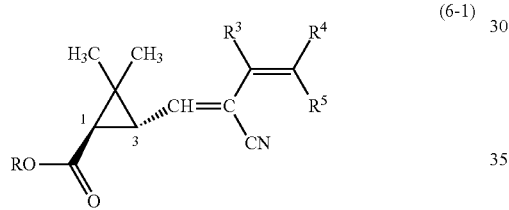

(6-1)

(wherein R, $R^3$, $R^4$ and $R^5$ have the same meanings as defined), and further hydrolyzing the obtained compound in the presence of a base.

The compound represented by the formula (6-1) can be usually produced by reacting in a polar solvent at a temperature within a range from 0° C. to 80° C.; and preferably from 0° C. to 30° C., using the nitrile compound represented by the formula (5) in the amount of 1.0 to 1.5 mol and a base in the mount of 1 to 10 mol, based on 1 mol of the caronaldehyde ester derivative represented by the formula (4-1). Examples of the base include carbonates such as potassium carbonate and sodium carbonate; and alkali metal compounds such as sodium hydride. Examples of the polar solvent include acid amides such as N,N-dimethylformamide; and sulfoxide such as dimethyl sulfoxide.

After completion of the reaction, the reaction mixture is subjected to a post-treatment operation of adding water, followed by extraction with an organic solvent and further drying and concentration of the organic layer, and thus the compound represented by the formula (6-1) can be obtained.

In the step of hydrolyzing the compound represented by the formula (6-1), the carboxylic acid compound represented by the formula (3-1) can be usually produced by reacting in a solvent at a temperature of 0° C. to 80° C., and preferably 0° C. to 30° C., using a base in the amount of 1 to 10 mol based on mol of the compound represented by the formula (6-1). Examples of the base include carbonic acid alkali metal salts such as potassium carbonate and sodium carbonate; and alkali metal compounds such as sodium hydride. Examples of the solvent include ethers such as tetrahydrofuran; alcohols such as methanol; water; and a mixture thereof.

After completion of the reaction, the reaction solution is subjected to a post-treatment operation of acidifying, followed by extraction with an organic solvent and further drying and concentration of the organic layer, and thus the carboxylic acid compound represented by the formula (3-1) can be obtained.

Among the carboxylic acid compound represented by the formula (3), a carboxylic acid compound represented by the formula (3-2) in which relative configuration of the substituent at the 1-position of the cyclopropane ring and the substituent at the 3-position of the cyclopropane ring is cis configuration can be produced, for example, by the following process.

That is, the carboxylic acid compound represented by the formula (3-2):

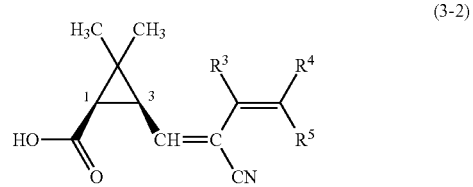

(3-2)

(wherein $R^3$, $R^4$ and $R^5$ have the same meanings as defined above), can be produced by reacting a caronaldehyde ester derivative represented by the formula (4-2):

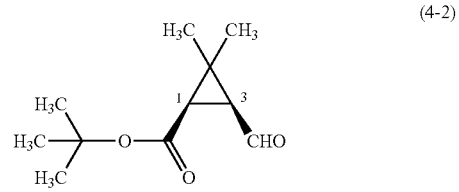

(4-2)

with the nitrile derivative represented by the formula (5):

(5)

(wherein $R^3$, $R^4$ and $R^5$ have the same meanings as defined above), in the presence of a base to obtain a compound represented by the formula (6-2):

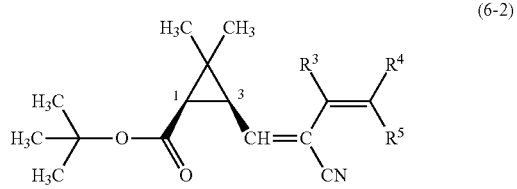

(6-2)

(wherein $R^3$, $R^4$ and $R^5$ have the same meanings as defined above), and heating the obtained compound in the presence of an acid catalyst.

The compound represented by the formula (6-2) can be usually produced by reacting in a polar solvent at a temperature of 0° C. to 80° C., and preferably 0° C. to 30° C., using the nitrile compound represented by the formula (5) in the amount of 1.0 to 1.5 mol and a base in the amount of 1 to 10 mol, based on 1 mol of the caronaldehyde ester derivative represented by the formula (4-2). Examples of the base include carbonates such as potassium carbonate and sodium carbonate; and alkali metal compounds such as sodium hydride. Examples of the polar solvent include acid amides such as N,N-dimethylformamide; and sulfoxides such as dimethyl sulfoxide.

After completion of the reaction, the reaction mixture is subjected to a post-treatment operation of adding water, followed by extraction with an organic solvent and further drying and concentration of the organic layer, and thus the compound represented by the formula (6-2) can be obtained.

In the step of producing the compound represented by the formula (3-2) from the compound represented by the formula (6-2), the reaction is carried out at a reaction temperature of usually 50° C. to 150° C. (50° C. to a boiling point of the solvent in a case a boiling point of the solvent is lower than 150° C.), using an acid catalyst in the amount of 0.005 to 0.05 mol based on 1 mol of the compound represented by the formula (6-2), and thus the carboxylic acid compound represented by the formula (3-2) can be produced. Examples of the acid catalyst include p-toluenesulfonic acid and the like. Examples of the solvent include ethers such as tetrahydrofuran; hydrocarbons such as toluene; and a mixture thereof.

After completion of the reaction, the carboxylic acid compound represented by the formula (3-2) can be obtained by subjecting to a post-treatment operation of drying and concentrating of the organic layer.

The caronaldehyde ester derivative represented by the formula (4-1) is a compound described in Tetrahedron 45, 3039-3052 (1989).

The caronaldehyde ester derivative represented by the formula (4-2) is a compound described in Journal of American Chemical Society, 1982, 104, 4282-4283.

The nitrile compound represented by the formula (5) can be synthesized according to a known method such as described in Journal of American Chemical Society, 2008, 130, 3734.

Examples of pests on which the compound of the present invention has a control effect include harmful arthropod pests such as harmful insects and harmful acarines, and more specifically, the following pests.

Hemiptera: planthoppers such as *Laodelphax striatellus*, *Nilaparvata lugens*, and *Sogatella furcifera*, leafhoppers such as *Nephotettix cincticeps*, and *Nephotettix virescens*, aphids such as *Aphis gossypii*, and *Myzus persicae*, plant bugs such as *Nezara antennata*, *Riptortus clavetus*, *Eysarcoris lewisi*, *Eysarcoris parvus*, *Plautia stali*, and Halyomorpha mista, white flies such as *Trialeurodes vaporariorum*, *Bemisia tabaci*, and *Bemisia* argentifolii, scales such as *Aonidiella aurantii*, *Comstockaspis perniciosa*, *Unaspis* citri, Ceroplastes rubens, and *Icerya purchasi*, lace bugs, bed bugs such as Cimex lectularius, jumping plantlice and so on;

Lepidoptera: Pyralidae such as *Chilo suppressalis*, *Cnaphalocrocis medinalis*, *Notarcha derogata*, and *Plodia interpunctella*, *Spodoptera litura*, *Pseudaletia separata*, Noctuidae such as *Trichoplusia* spp., *Heliothis* spp., and *Earias* spp., Pieridae such as *Pieris rapae*, Tortricidae such as *Adoxopheys* spp., *Grapholita molesta*, *Adoxophyes orana fasciata*, and *Cydia pomonella*, Carposimidae such as *Carposina niponensis*, Lyonetiidae such as *Lyonetia* spp., Lymantriidae such as *Lymantria* spp., Lymantriidae such as *Euproctis* spp., Yponameutidae such as *Plutella xylostella*, Gelechiidae such as *Pectinophora gossypiella*, Arctiidae such as *Hyphantria cunea*, Tineidae such as Tinea translucens, and *Tineola* bisselliella, and so on;

Diptera: *Culex* spp. such as *Culex* pipiens pallens, *Culex* tritaeniorhynchus, and *Culex quinquefasciatus*, *Aedes* spp. such as *Aedes aegypti*, and *Aedes albopictus*, *Anopheles* spp. such as *Anopheles sinensis*, and *Anopheles gambiae*, Chironomidae, Muscidae such as *Musca domestica*, and Muscina stabulans, Calliphoridae, Sarcophagidae, little housefly, Anthomyiidae such as *Delia platura*, and *Delia antiqua*, Tephritidae, Drosophilidae, Phoridae such as *Megaselia spiracularis*, *Clogmia albipunctata*, Psychodidae, Simuliidae, Tabanidae, Stomoxyidae, Agromyzidae, and so on;

Coleoptera: *Diabrotica* spp. such as *Diabrotica virgifera* virgifera, and *Diabrotica undecimpunctata* howardi, Scarabaeidae such as *Anomala cuprea*, and *Anomala* rufocuprea, Curculionidae such as *Sitophilus zeamais*, *Lissorhoptrus oryzophilus*, and Callosobruchuys chienensis, Tenebrionidae such as *Tenebrio molitor*, and *Tribolium castaneum*, Chrysomelidae such as *Oulema oryzae*, *Aulacophora femoralis*, *Phyllotreta striolata*, and *Leptinotarsa decemlineata*, Dermestidae such as Dermestes maculates, Anobiidae, *Epilachna* spp. such as *Epilachna* vigintioctopunctata, Lyctidae, Bostrychidae, Ptimidae, Cerambycidae, Paederus fuscipes, and so on;

Blattodea: *Blattella germanica*, *Periplaneta fuliginosa*, *Periplaneta americana*, *Periplaneta brunnea*, *Blatta orientalis*, and so on;

Thysanoptera: *Thrips palmi*, *Thrips tabaci*, *Frankliniella occidentalis*, *Frankliniella* intonsa, and so on;

Hymenoptera: Formicidae such as *Monomorium* pharaosis, *Formica* fusca japonica, Ochetellus glaber, Pristomyrmex pungens, Pheidole noda, and Linepithema humile, long-legged wasps such as Polistes chinensis antennalis, Polistes jadwigae, and Polistes rothneyi, Vespidae such as *Vespa mandarinia japonica*, *Vespa simillima*, *Vespa analis* insularis, *Vespa crabro* flavofasCiata, and *Vespa ducalis*, Bethylidae, Xylocopa, Pompilidae, Sphecoidae, mason wasp, and so on;

Orthoptera: mole crickets, grasshoppers, etc.;

Shiphonaptera: *Ctenocephalides felis*, *Ctenocephalides* canis, *Pulex irritans*, *Xenopsylla* cheopis, and so on;

Anoplura: Pediculus humanus corporis, Phthirus pubis, Haematopinus eurysternus, Dalmalinia ovis, and so on;

Isoptera: *Reticulitermes* spp. such as *Reticulitermes speratus*, *Coptotermes formosanus*, *Reticulitermes flavipes*, *Reticulitermes hesperus*, *Reticulitermes virginicus*, *Reticulitermes tibialis*, and Heterotermes aureus, *Incisitermes* spp. such as *Incisitermes* minor, and *Zootermopsis* spp. such as *Zootermopsis* nevadensis, and so on;

Acarina: Tetranychidae such as *Tetranychus urticae*, *Tetranychus kanzawai*, *Panonychus citri*, *Panonychus ulmi*, and *Oligonychus* spp., Eriophyidae such as *Aculops pelekassi*, and *Aculus* schleohtendali, Tarsonemidae such as *Polyphagotarsonemus* latus, Tendipalpidae, Tuckerellidae, Ixodidae such as Haemaphysalis longicornis, Haemaphysalis flava, Dermacentor variabilis, Ixodes ovatus, Ixodes persulcatus), Ixodes scapularis, Boophilus microplus, Amblyomma americanum, and Rhipicephalus sanguineus, Acaridae such as Tyrophagus putrescentiae, Dermanyssidae such as *Dermatophagoides farinae*, *Dermatophagoides* ptrenyssnus, Cheyletidae such as Cheyletus-eruditus, Cheyletus malaccensis, and Cheyletus moorei, chicken mite such as Ornithonyssus bacoti, Ornithonyssus sylvairum, and Dermanyssus gallinae, Trombiculidae such as Leptotrombidium akamushi, and so on;

Araneae: Japanese foliage spider (Chiracanthium japonicum), redback spider (Latrodectus hasseltii), Nephila clavata (Tetragnathidae), Cyclosa octotuberculata, St. Andrew's cross spider (Argiope amoena), Wasp sopider (Argiope bruennichii), orb-weaving spider (Araneus ventricosus), grass spider (Agelena silvatica), wolf spider (Pardosa astrigera), dock spider (Dolomedes sulfurous), Carrhotus xanthogramma, common house spider (Achaearanea tepidariorum), Coelotes insidiosus, jumping spider (Salticidae), huntsman spider (Heteropoda venatoria), etc.;

Chilopoda: centipedes such as house centipede (Thereuonema hilgendorfi), Scolopendra subspinipes, Scolopendra subspinipes japonica, Scolopocryptops rubiginosus, Bothropolys asperatus, etc.;

Diplopoda: millipedes such as garden millipede (Oxidus gracilis), garden millipede (Nedyopus tambanus), train millipede (Parafontaria laminate), train millipede (Parafontaria laminata armigera), Parafontaria acutidens, Epanerchodus orientalis, etc.;

Isopoda: sow bugs such as Porcellionides pruinosus (Brandt), Porcellio scaber Latreille, pill bugs such as common pill bug (Armadillidium vulgare), sea louses such as wharf roach (Ligia exotica), etc.;

Gastropoda: tree slug (Limax marginatus), yellow slug (Limax flavus), etc.

The pest control agent of the present invention contains the compound of the present invention and an inert carrier. The pest control agent of the present invention is usually formed into formulations described below. Examples of the formulation include an oil solution, an emulsifiable concentrate, a wettable powder, a flowable formulation (e.g., an aqueous suspension, or an aqueous emulsion), a microcapsule, a dust, a granule, a tablet, an aerosol, a carbon dioxide formulation, a heat transpiration formulation (e.g., an insecticidal coil, an electric insecticidal mat, or a liquid absorbing core-type heat transpiration pesticide), a piezo insecticidal formulation, a heat fumigant (e.g., a self combustion-type fumigant, a chemical reaction-type fumigant, or a porous ceramic plate fumigant), an unheated transpiration formulation (e.g., a resin transpiration formulation, a paper transpiration formulation, an unwoven fabric transpiration formulation, a knit fabric transpiration formulation, or a sublimating tablet), an aerosol formulation (e.g., a fogging formulation), a direct contact formulation (e.g., a sheet-shaped contact formulation, a tape-shaped contact formulation, or a net-shaped contact formulation), an ULV formulation and a poison bait Examples of the method for formulation include the following methods.

(1) A method comprising mixing the compound of the present invention with a solid carrier, a liquid carrier, a gaseous carrier or a poison bait, followed by addition of a surfactant and other auxiliary agents for formulation, and if necessary, further processing.

(2) A method comprising impregnation of a base material containing no active ingredient with the compound of the present invention.

(3) A method comprising mixing the compound of the present invention and a base material, followed by subjecting the mixture to mold processing.

These formulations usually contain 0.001 to 98% by weight of the compound of the present invention, depending on formulation forms.

Examples of the solid carrier used in the formulation include fine powders or granules of clays (e.g., kaolin clay, diatomaceous earth, bentonite, Fubasami clay, or acid white clay), synthetic hydrated silicon oxide, talc, ceramics, other inorganic minerals (e.g., sericite, quartz, sulfur, active carbon, calcium carbonate, or hydrated silica) and fine powder and granulated substances such as chemical fertilizers (e.g., ammonium sulfate, ammonium phosphate, ammonium nitrate, ammonium chloride, or urea); substances that are solid at room temperature (e.g., 2,4,6-triisopropyl-1,3,5-trioxane, naphthalene, p-dichlorobenzene, or camphor, adamantine); as well as felt, fiber, fabric, knit, sheet, paper, thread, foam, porous material and multi-filament comprising one or more substances selected from the group consisting of wool, silk, cotton, hemp, pulp, synthetic resins (e.g., polyethylene resins such as low density polyethylene, straight chain low density polyethylene and high density polyethylene; ethylene-vinyl ester copolymers such as an ethylene-vinyl acetate copolymer; ethylene-methacrylate copolymers such as an ethylene-methyl methacrylate copolymer and an ethylene-ethyl methacrylate copolymer; ethylene-acrylate copolymers such as an ethylene-methyl acrylate copolymer and an ethylene-ethyl acrylate copolymer; ethylene-vinylcarboxylic acid copolymers such as an ethylene-acrylic acid copolymer; ethylene-tetracyclododecene copolymers; polypropylene resins such as a propylene homopolymer and a propylene-ethylene copolymer; poly-4-methylpentene-1, polybutene-1, polybutadiene, polystyrene; acrylonitrile-styrene resin; acrylonitrile-butadiene-styrene resins; styrene elastomers such as a styrene-conjugated diene block copolymer and a hydrogenated styrene-conjugated diene block copolymer; fluorine resins; acrylic resins such as methyl polymethacrylate; polyamide resins such as nylon 6 and nylon 66; polyester resins such as polyethylene terephthalate, polyethylene naphthalate, polybutylene terephthalate and polycyclohexylene dimethylene terephthalate; or porous resins such as polycarbonate, polyacetal, polyacryl sulfone, polyarylate, hydroxybenzoic acid polyester, polyetherimide, polyester carbonate, polyphenylene ether resins, polyvinyl chloride, polyvinylidene chloride, polyurethane, foamed polyurethane, foamed polypropylene and foamed ethylene), glass, metal and ceramics.

Examples of the liquid carrier include aromatic or aliphatic hydrocarbons (e.g., xylene, toluene, alkylnaphthalene, phenylxylylethane, kerosene, light oil, hexane, or cyclohexane), halogenated hydrocarbons (e.g., chlorobenzene, dichloromethane, dichloroethane, or trichloroethane), alcohols (e.g., methanol, ethanol, isopropyl alcohol, butanol, hexanol, benzyl alcohol, or ethylene glycol), ethers (e.g., diethyl ether, ethylene glycol dimethyl ether, diethylene glycol monomethyl ether, diethylene glycol monoethyl ether, propylene glycol monomethyl ether, tetrahydrofuran, or dioxane), esters (e.g., ethyl acetate, or butyl acetate), ketones (e.g., acetone, methyl ethyl ketone, methyl isobutyl ketone, or cyclohexanone), nitriles (e.g., acetonitrile, or isobutyronitrile), sulfoxides (e.g., dimethyl sulfoxide), acid amides (e.g., N,N-dimethylformamide, N,N-dimethylacetamide, or N-methylpyrrolidone), alkylidene carbonate (e.g., propylene carbonate), vegetable oils (e.g., soybean oil, or cottonseed oil), plant essential oils (e.g., orange oil, hyssop oil, or lemon oil), and water.

Examples of the gaseous carrier include butane gas, chlorofluorocarbon, liquefied petroleum gas (LPG), dimethyl ether and carbon dioxide.

Examples of the surfactant include alkyl sulfate, alkyl sulfonate, alkylaryl sulfonate, alkylaryl ethers, polyoxyethylenated alkylaryl ethers, polyethylene glycol ethers, polyhydric alcohol esters and sugar alcohol derivatives.

Examples of the other auxiliary agents for formulation include a binder, a dispersant and a stabilizer. Specifically, there are, for example, casein, gelatin, polysaccharides (e.g., starch, gum arabic, cellulose derivatives, or alginic acid), lignin derivatives, bentonite, saccharides, synthetic water-soluble polymers (e.g., polyvinyl alcohol, or polyvinyl pyrrolidone), polyacrylic acid, BHT (2,6-di-tert-butyl-4-methylphenol) and BHA (a mixture of 2-tert-butyl-4-methoxyphenol and 3-tert-butyl-4-methoxyphenol).

Examples of a base material for the insecticidal coil include a mixture of vegetable powder such as wood flour and lees powder, and a binder such as incense material powder, starch and gluten.

Examples of a base material for the electric insecticidal mat include a plate obtained by hardening cotton linter and a plate obtained by hardening fibrils of a mixture of cotton linter and pulp.

Examples of a base material for the self combustion-type fumigant include combustible exothermic agents such as nitrate, nitrite, guanidine salt, potassium chlorate, nitrocellulose, ethylcellulose and wood flour, thermal decomposition stimulants such as alkali metal salt, alkaline earth metal salt, dichromate and chromate, oxygen carriers such as potassium nitrate, combustion-supporting agents such as melamine and flour starch, extenders such as diatomaceous earth, and binders such as synthetic glue.

Examples of a base material for the chemical reaction-type fumigant include exothermic agents such as alkali metal sulfide, polysulfide, hydrosulfide and calcium oxide, catalytic agents such as a carbonaceous material, iron carbide and active white clay, organic foaming agents such as azodicarbonamide, benzenesulfonylhydrazide, dinitropentamethylenetetramine, polystyrene and polyurethane, and fillers such as strips of natural fiber and synthetic fiber.

Examples of a resin used as a base material of the resin transpiration formulation include polyethylene resins such as low density polyethylene, straight chain low density polyethylene and high density polyethylene; ethylene-vinyl ester copolymers such as an ethylene-vinyl acetate copolymer; ethylene-methacrylate copolymers such as an ethylene-methyl methacrylate copolymer and an ethylene-ethyl methacrylate copolymer; ethylene-acrylate copolymers such as an ethylene-methyl acrylate copolymer and an ethylene-ethyl acrylate copolymer; ethylene-vinylcarboxylic acid copolymers such as an ethylene-acrylic acid copolymer; ethylene-tetracyclododecene copolymers; polypropylene resins such as a propylene copolymer and a propylene-ethylene copolymer; poly-4-methylpentene-1, polybutene-1, polybutadiene, polystyrene, acrylonitrile-styrene resins; acrylonitrile-butadiene-styrene resins; styrene elastomers such as a styrene-conjugated diene block copolymer and a hydrogenated styrene-conjugated diene block copolymer; fluorine resins; acrylic resins such as methyl polymethacrylate; polyamide resins such as nylon 6 and nylon 66; polyester resins such as polyethylene terephthalate, polyethylene naphthalate, polybutylene butalate and polycyclohexylene dimethylene terephthalate; polycarbonate, polyacetal, polyacryl sulfone, polyarylate, hydroxybenzoic acid polyester, polyetherimide, polyester carbonate, polyphenylene ether resin, polyvinyl chloride, polyvinylidene chloride and polyurethane. These base materials may be used alone or as a combination of two or more kinds. If necessary, a plasticizer such as phthalate esters (e.g., dimethyl phthalate, dioctyl phthalate, etc.), adipic acid esters and stearic acid may be added to these base materials. The resin transpiration formulation can be prepared by mixing the compound of the present invention with the base material, kneading the mixture, followed by molding it by injection molding, extrusion molding or pressure molding. The resultant resin formulation can be subjected to further molding or cutting procedure, if necessary, to be processed into shapes such as a plate, film, tape, net or string shape.

These resin formulations can be processed into animal collars, animal ear tags, sheet products, trap strings, gardening supports and other products.

Examples of a base material for the poison bait include bait ingredients such as grain powder, vegetable oil, saccharide and crystalline cellulose, antioxidants such as dibutylhydroxytoluene and nordihydroguaiaretic acid, preservatives such as dehydroacetic acid, accidental ingestion inhibitors for children and pets such as a chili powder; insect attraction fragrances such as cheese flavor, onion flavor and peanut oil.

The pest control method of the present invention usually conducted by applying an effective amount of the compound of the present invention to a pest or a habitat thereof (e.g. plant bodies, soil, the interior of a house, animal bodies, the interior of a car, or outdoor open space) in a form of a pest control agent of the present invention.

A method for applying the pest control agent of the present invention includes the following methods, and appropriately selected depending on the form of the pest control agent of the present invention, the application area and so on.

(1) A method comprising applying a pest control agent of the present invention as it is to a pest or a habitat of the pest.

(2) A method comprising diluting a pest control agent of the present invention with a solvent such as water, and then spraying the dilution to a pest or a habitat of the pest. In this method, the pest control agent of the present invention is usually formulated into an emulsifiable concentrate, a wettable powder, a flowable formulation, a microcapsule or the like. The formulation is usually diluted so that the concentration of the compound of the present invention can be 0.1 to 10,000 ppm.

(3) A method comprising heating a pest control agent of the present invention at a habitat of a pest, thereby allowing an active ingredient to volatilize and diffuse from the pest control agent.

In this case, any of the amount and concentration of application of the compound of the present invention can be appropriately determined depending on the form, application period, application area, application method, kind of a pest, damage to be incurred and so on.

When the compound of the present invention is used for prevention of epidemics, the amount to be applied is usually from 0.0001 to 1,000 mg/m$^3$ of the compound of the present invention in the case of applying to a space, and from 0.0001 to 1,000 mg/m$^2$ of the compound of the present invention in the case of applying to a plane. An insecticidal coil or an electric insecticidal mat is applied by heating to volatilize and diffuse an active ingredient, depending on the form of the formulation. A resin transpiration formulation, a paper transpiration formulation, an unwoven fabric transpiration formulation, a knit fabric transpiration formulation or a sublimating tablet are allowed to stand as it is in a space to be applied, and placed under air blowing.

When the pest control agent of the present invention is applied to a space for the purpose of prevention of epidemics, examples of the space include a closet, a Japanese cabinet, a Japanese chest, a cupboard, a toilet, a bathroom, a shed, a living room, a dining room, a garage, the interior of a car and so on. The pest control agent can be also applied to outdoor open space.

When the pest control agent of the present invention is used for controlling external parasites of livestock such as cows, horses, pigs, sheep, goats and chickens and small animals such as dogs, cats, rats and mice, the pest control agent of the present invention can be applied to the animals by a known method in the veterinary field. Specifically, when systemic control is intended, the pest control agent of the present invention is administered to the animals as a tablet, a mixture with feed or a suppository, or by injection (including intramuscular, subcutaneous, intravenous and intraperitoneal injections). On the other hand, when non-systemic control is intended, the pest control agent of the present invention is applied to the animals by means of spraying of the oil solution or aqueous solution, pour-on or spot-on treatment, or washing of the animal with a shampoo formulation, or by putting a collar or ear tag made of the resin transpiration formulation to the animal. In the case of administering to an animal body, the dosage of the compound of the present invention is usually in the range from 0.1 to 1,000 mg per 1 kg of an animal body weight.

When the pest control agent of the present invention is used for controlling a pest in the agricultural field, the amount can widely vary depending on the application period, application area, application method and other factors, and is usually in the range from 1 to 10,000 g in terms of the compound of the present invention per 10,000 $m^2$. When the pest control agent of the present invention is formulated into an emulsifiable concentrate, a wettable powder, a flowable formulation and so on, the pest control agent is usually applied after diluting with water so that the concentration of the active ingredient becomes 0.01 to 10,000 ppm, and a granule or a dust is usually applied as it is.

These formulations or water dilutions of the formulations may be directly sprayed over pests or plants such as crop plants to be protected from pests, or may be used in the soil treatment for the control of pests which inhabit the soil of the cultivated land.

Application can also be conducted by a method of directly winding the resin formulation formed into sheet-shaped, or string- or cord-shaped formulation around plants, disposing the formulation in the neighborhood of plants, or spreading the formulation on the soil surface at the root.

The compound of the present invention can be used as a pest control agent in cultivating field such as farm, paddy field, lawn or orchard, or non-cultivating field. The compound of the present invention can control pests inhabiting the cultivating field in the cultivating field where the following "plant crops" are cultivated.

Agricultural crops: corn, rice, wheat, barley, rye, oat, sorghum, cotton, soybean, peanut, sarrazin, sugar beet, rapeseed, sunflower, sugar cane, tobacco, etc.;

Vegetables: Solanaceae vegetables (eggplant, tomato, green pepper, hot pepper, potato etc.), Cucurbitaceae vegetables (cucumber, pumpkin, zucchini, watermelon, melon etc.), Cruciferae vegetables (Japanese radish, turnip, horseradish, kohlrabi, Chinese cabbage, cabbage, brown mustard, broccoli, cauliflower etc.), Compositae vegetables (burdock, garland chrysanthemum, artichoke, lettuce etc.), Liliaceae vegetables (Welsh onion, onion, garlic, asparagus etc.), Umbelliferae vegetables (carrot, parsley, celery, parsnip etc.), Chenopodiaceae vegetables (spinach, Swiss chard etc.), Labiatae vegetables (Japanese basil, mint, basil etc.), strawberry, sweat potato, yam, aroid, etc.;

Fruit trees: pomaceous fruits (apple, common pear, Japanese pear, Chinese quince, quince etc.), stone fleshy fruits (peach, plum, nectarine, Japanese plum, cherry, apricot, prune etc.), citrus plants (Satsuma mandarin, orange, lemon, lime, grapefruit etc.), nuts (chestnut, walnut, hazel nut, almond, pistachio, cashew nut, *macadamia* nut etc.), berry fruits (blueberry, cranberry, blackberry, raspberry etc.), grape, persimmon, olive, loquat, banana, coffee, date, coconut palm, oil palm, etc.;

Trees other than fruit trees: tea, mulberry, woody plants (azalea, camellia, hydrangea, sasanqua, Illicium religiosum, cherry tree, tulip tree, crape myrtle, fragrant olive etc.), street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, horse-chestnut etc.), sweet viburnum, *Podocarpus macrophyllus*, Japanese cedar, Japanese cypress, croton, spindle tree, Chainese howthorn, etc.

Lawn: zoysia (Japanese lawn grass, mascarene grass, etc.), Bermuda grass (Cynodon dactylon, etc.), bent grass (creeping bent grass, *Agrostis stolonifera, Agrostis tenuis*, etc.), bluegrass (Kentucky bluegrass, rough bluegrass, etc.), fescue (tall fescue, chewing fescue, creeping fescue, etc.), ryegrass (darnel, perennial ryegrass, etc.), cocksfoot, timothy grass, etc.;

Others: flowers (rose, carnation, chrysanthemum, Eustoma grandiflorum Shinners (prairie gentian), gypsophila, gerbera, pot marigold, salvia, petunia, verbena, tulip, aster, gentian, lily, pansy, cyclamen, orchid, lily of the valley, lavender, stock, ornamental kale, primula, poinsttia, gladiolus, cattleya, daisy, verbena, cymbidium, begonia, etc.), bio-fuel plants (Jatropha, safflower, gold-of-pleasure, switchgrass, Miscanthus, ribbon grass, giant reed, kenaf, cassaya, willow, etc.), foliage plant; etc.

The above "plant crops" include gene transgenic plant crops.

The compound of the present invention can be mixed with or can be used in combination with other insecticide, acaricide, nematocide, soil pest control agent, fungicide, herbicide, plant growth regulating agent, repellent, synergist, fertilizer, or soil modifier.

Examples of active ingredient of such the insecticide and acaricide include:

(1) Synthetic Pyrethroid Compounds:

acrinathrin, allethrin, beta-cyfluthrin, bifenthrin, cycloprothrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, 2,3,5,6-tetrafluoro-4-methylbenzyl=2,2-dimethyl-3-(1-propenyl)cyclopropane carboxylate, 2,3,5,6-tetrafluoro-4-(methoxymethyl)benzyl=2,2-dimethyl-3-(2-methyl-1-propenyl)cyclopropane carboxylate, 2,3,5,6-tetrafluoro-4-(methoxymethyl)benzyl=2,2,3,3-tetramethylcyclopropane carboxylate, and so on;

(2) Organic Phosphorous Compounds:

acephate, Aluminium phosphide, butathiofos, cadusafos, chlorethoxyfos, chlorfenvinphos, chlorpyrifos, chlorpyrifos-methyl, cyanophos: CYAP, diazinon, DCIP(dichlorodiisopropyl ether), dichlofenthion:ECP, dichlorvos:DDVP, dimethoate, dimethylvinphos, disulfoton, EPN, ethion, ethoprophos, etrimfos, fenthion:MPP, fenitrothion:MEP, fosthiazate, formothion, Hydrogen phosphide, isofenphos, isoxathion, malathion, mesulfenfos, methidathion:DMTP, monocrotophos, naled:BRP, oxydeprofos:ESP, parathion, phosalone, phosmet:PMP, pirimiphos-methyl, pyridafenthion, quinalphos, phenthoate:PAP, profenofos, propaphos, prothiofos, pyraclorfos, salithion, sulprofos, tebupirimfos, temephos, tetrachlorvinphos, terbufos, thiometon, trichlorphon:DEP, vamidothion, phorate, cadusafos, and so on;

(3) Carbamate Compounds:
alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb:MIPC, metolcarb, methomyl, methiocarb, NAC, oxamyl, pirimicarb, propoxur:PHC, XMC, thiodicarb, xylylcarb, aldicarb, and so on;
(4) Nereistoxin Compounds:
cartap, bensultap, thiocyclam, monosultap, bisultap, and so on;
(5) Neonicotinoid Compounds:
imidacloprid, nitenpyram, acetamiprid, thiamethoxam, thiacloprid, dinotefuran, clothianidin, and so on;
(6) Benzoylurea Compounds:
chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, triazuron, and so on;
(7) Phenylpyrazole Compounds:
acetoprole, ethiprole, fipronil, vaniliprole, pyriprole, pyrafluprole, and so on;
(8) Bt Toxin Insecticides:
Live spores derived from and crystal toxins produced from *Bacillus* thuringiesis and a mixture thereof;
(9) Hydrazine Compounds:
chromafenozide, halofenozide, rnethoxyfenozide, tebufenozide, and so on;
(10) Organic Chlorine Compound:
aldrin, dieldrin, dienochlor, endosulfan, methoxychlor, and so on;
(11) Natural Insecticides:
machine-oil, nicotine-sulfate;
(12) Other Insecticides:
avermectin-B, bromopropylate, buprofezin, chlorphenapyr, cyromazine, D-D(1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad; triazamate, flubendiamide, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, Sulfur, metaflumizone, spirotetramat, pyrifluquinazone, spinetoram, chlorantraniliprole, tralopyril, and so on.

Examples of the active ingredient of the repellent include N,N-diethyl-m-toluamide, limonene, linalool, citronellal, menthol, menthone, hinokitiol, geraniol, eucalyptol, indoxacarb, carane-3,4-diol, MGK-R-326, MGK-R-874 and BAY-KBR-3023.

Examples of the active ingredient of the synergist include'5-[2-(2-butoxyethoxy)ethoxymethyl]-6-propyl-1,3-benzodioxol, N-(2-ethylhexyl)bicyclo[2.2.1]hept-5-ene-2,3-dicarboxylmide, octachlorodipropylether, thiocyanoacetic acidisobornyl, N-(2-ethylhexyl)-1-isopropyl-4-methylbicyclo[2.2.2]oct-5-ene-2,3-dicarboxylmide.

EXAMPLES

Hereinafter, the present invention will be described in more detail by way of Production Examples, Formulation Examples and Test Examples, but the present invention is not limited thereto.

First, Production Examples of the compound of the present invention will be described.

Production Example 1

To a chloroform solution (10 mL) of 4-methoxymethyl-2,3,5,6-tetrafluorobenzyl alcohol (594 mg, 2.65 mmol) and (1R)-trans-3-[(1Z)-2-cyano-1,3-butadienyl]-2,2-dimethyl-cyclopropanecarboxylic acid (478 mg, 2.50 mmol), 1-ethyl-3-(3-dimethylaminopropyl)carbodiimide hydrochloride (516 mg, 2.70 mmol) and 4-dimethylaminopyridine (15 mg) were added. After stirring at room temperature for 3 hours, water was poured into the reaction solution and the solution was extracted with ethyl acetate. The organic layer was dried over magnesium sulfate and then concentrated under reduced pressure condition, and the residue was subjected to silica gel column chromatography to obtain 771 mg of 4-methoxymethyl-2,3,5,6-tetrafluorobenzyl=(1R)-trans-3-[(1Z)-2-cyano-1,3-butadienyl]-2,2-dimethylcyclopropane carboxylate (hereinafter referred to as the present invention compound (1)) represented by the following formula:

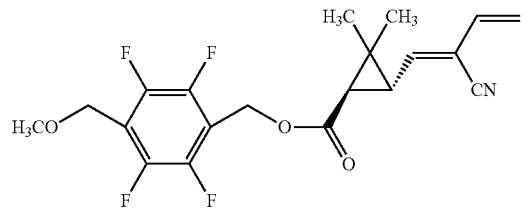 [SMILES: C=C/C(C#N)=C/[C@@H]1[C@@H](C(=O)OCc2c(F)c(F)c(COC)c(F)c2F)C1(C)C]

Pale yellow liquid: $^1$H-NMR (CDCl$_3$, TMS) δ (ppm): 1.21 (s, 3H), 1.35 (s, 3H), 1.81 (d, 1H), 2.54 (m, 1H), 3.41 (s, 3H), 4.58 (d, 2H), 5.26 (s, 2H), 5.28 (d, 1H), 5.56 (d, 1H), 5.95 (d, 1H), 6.24 (dd, 1H)

Production Example 2

4-methoxymethyl-2,3,5,6-tetrafluorobenzyl alcohol (560 mg, 2.50 mmol) was dissolved in tetrahydrofuran (10 mL) and 0.35 mL of pyridine was added. To the solution, tetrahydrofuran solution (5 mL) of (1R)-trans-3-[(1Z,3E)-2-cyano-1,3-pentadienyl]-2,2-dimethylcyclopropanecarboxylic acid chloride (Z/E=85/15) (570 mg, 2.55 mmol) was added under ice cooling. After stirring. at room temperature for 12 hours, water was poured into the reaction solution and the solution was extracted with ethyl acetate. The organic layer was washed in turn with 5% hydrochloric acid, saturated sodium bicarbonate water and saturated brine, and then dried over magnesium sulfate. After concentration under reduced pressure condition, the residue was subjected to silica gel column chromatography to obtain 760 mg of 4-methoxymethyl-2,3,5,6-tetrafluorobenzyl=(1R)-trans-3-[(1Z,3E)-2-cyano-1,3-pentadienyl]-2,2-dimethylcyclopropane carboxylate (hereinafter referred to as the present invention compound (2)) represented by the following formula:

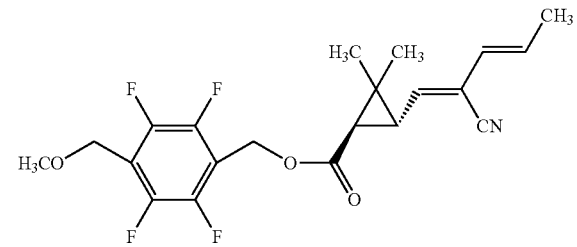

Colorless liquid: $^1$H-NMR (CDCl$_3$, TMS) δ (ppm): 1.21 (s, 3H), 1.34 (s, 3H), 1.75 (d, 1H, J=5.6 Hz), 1.82 (d, 3H, J=6.8 Hz), 2.52 (dd, 1H, J=9.5, 5.3 Hz), 3.40 (s, 3H), 4.58 (s, 2H), 5.25 (s, 2H), 5.79 (d, 1H), 5.95 (d, 1H), 6.10 (m, 1H)

Specific examples of the compound of the present invention will be described below.

4-methyl-2,3,5,6-tetrafluorobenzyl=(1R)-trans-3-[(1Z,3E)-2-cyano-1,3-pentadienyl]-2,2-dimethylcyclopropane carboxylate represented by the following formula:

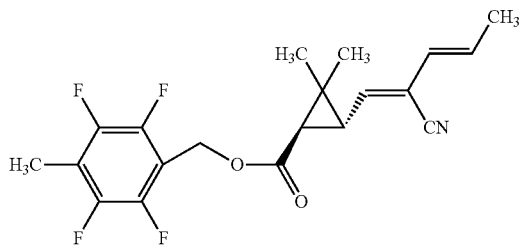 [SMILES: C/C=C/C(C#N)=C/[C@@H]1[C@@H](C(=O)OCc2c(F)c(F)c(C)c(F)c2F)C1(C)C]

4-methoxy-2,3,5,6-tetrafluorobenzyl=(1R)-trans-3-[(1Z,3E)-2-cyano-1,3-pentadienyl]-2,2-dimethylcyclopropane carboxylate represented by the following formula:

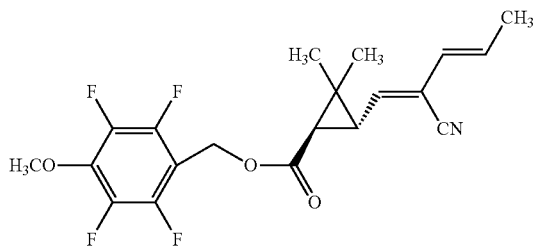 [SMILES: C/C=C/C(C#N)=C/[C@@H]1[C@@H](C(=O)OCc2c(F)c(F)c(OC)c(F)c2F)C1(C)C]

4-methylthiomethyl-2,3,5,6-tetrafluorobenzyl=(1R)-trans-3-[(1Z,3E)-2-cyano-1,3-pentadienyl]-2,2-dimethylcyclopropane carboxylate represented by the following formula:

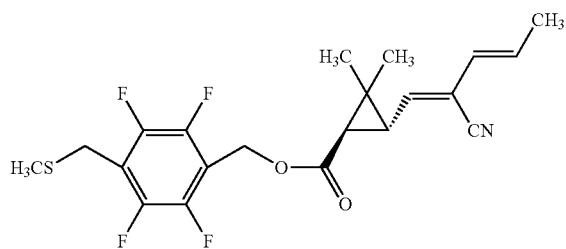

2,3,4,5,6-pentafluorobenzyl=(1R)-trans-3-[(1Z,3E)-2-cyano-1,3-pentadienyl)-2,2-dimethylcyclopropahe carboxylate represented by the following formula:

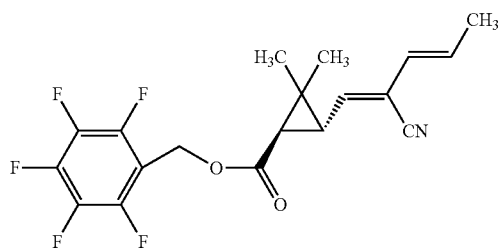 [SMILES: C/C=C/C(C#N)=C/[C@@H]1[C@@H](C(=O)OCc2c(F)c(F)c(F)c(F)c2F)C1(C)C]

Reference Production Example 1

Methyl=(1R)-trans-3-formyl-2,2-dimethylcyclopropane carboxylate (2.53 g, 16.2 mmol), 3-pentenonitrile (1.90 g, 23.5 mmol) and anhydrous potassium carbonate (3.22 g, 23.3 mmol) were added to 30 mL of N,N-dimethylformamide and the mixture was stirred at room temperature for 24 hours. The reaction solution was added to 100 mL of ice water and the solution was extracted twice with each 100 mL of ethyl acetate. The obtained ethyl acetate layers were combined, washed once with 50 mL of saturated brine and then dried over magnesium sulfate. After concentration under reduced pressure condition, the residue was subjected to silica gel column chromatography to obtain 0.94 g of methyl=(1R)-trans-3-[(1Z,3E)-2-cyano-1,3-pentadienyl]-2,2-dimethylcyclopropane carboxylate represented by the following formula:

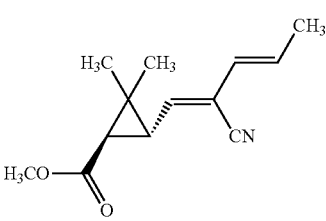 [SMILES: C/C=C/C(C#N)=C/[C@@H]1[C@@H](C(=O)OC)C1(C)C]

Colorless liquid: $^1$H-NMR (CDCl$_3$, TMS) δ (ppm): 1.22 (s, 3H), 1.35 (s, 3H), 1.75 (d, 1H, J=5.2 Hz), 1.82 (d, 3H, J=5.2 Hz), 2.5 (m, 1H, J=10.0, 5.2 Hz), 3.7 (s, 3H), 5.82 (d, 1H, J=10.0 Hz), 5.96 (d, 1H, J=16.8 Hz), 6.10 (m, 1H)

Reference Production Example 2

Methyl=(1R)-trans-3-[(1Z,3E)-2-cyano-1,3-pentadienyl]-2,2-dimethylcyclopropane carboxylate (502 mg, 2.29 mmol) was dissolved in a mixed liquid of 3 mL of methanol and 1 mL of water, and then potassium hydroxide (300 mg, 5.36 mmol) was added and the mixed solution was stirred at room temperature for 24 hours. The reaction solution was added to 20 mL of ice water and the solution was extracted with 20 mL of ethyl acetate. To the obtained aqueous layer, 5% hydrochloric acid was added until the pH became 2, and then the solution was extracted with 30 mL of ethyl acetate. The ethyl acetate layer was washed twice with 20 mL of saturated brine and then dried over magnesium sulfate. After concentration under reduced pressure condition, 452 mg of (1R)-trans-3-[(1Z,3E)-2-cyano-1,3-pentadienyl]-2,2-dimethylcyclopropanecarboxylic acid represented by the following formula:

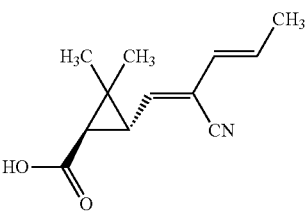

was obtained.

Colorless liquid: $^1$H-NMR (CDCl$_3$, TMS) δ (ppm): 1.23 (s, 3H), 1.38 (s, 3H), 1.76 (d, 1H, J=5.2 Hz), 1.82 (d, 3H, J=6.4 Hz), 2.54 (dd, 1H, J=10.0, 5.2 Hz), 5.82 (d, 1H, J=10.0 Hz), 5.97 (d, 1H, J=15.6 Hz), 6.11 (m, 1H)

Reference Production Example 3

Methyl=(1R)-trans-3-formyl-2,2-dimethylcyclopropane carboxylate (2.53 g, 16.2 mmol), 3-butenonitrile (3.62 g, 54.0 mmol) and anhydrous potassium carbonate (3.22 g, 23.3 mmol) were added to 30 mL of N,N-dimethylformamide and the mixture was stirred at room temperature for 24 hours. The reaction solution was added to 100 mL of ice water and the solution was extracted twice with each 100 mL of ethyl acetate. The ethyl acetate layers were combined, washed once with 50 mL of saturated brine and then dried over magnesium sulfate. After concentration under reduced pressure condition, the residue was subjected to silica gel column chromatography to obtain 0.37 g of methyl=(1R)-trans-3-[(1Z)-2-cyano-1,3-butadienyl]-2,2-dimethylcyclopropane carboxylate represented by the following formula:

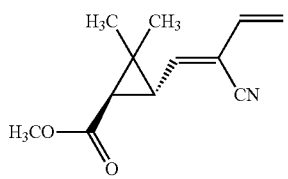

Colorless liquid: $^1$H-NMR (CDCl$_3$, TMS) δ (ppm): 1.24 (s, 3H), 1.35 (s, 3H), 1.81 (d, 1H, J=5.2 Hz), 2.54 (dd, 1H, J=10.4, 5.2 Hz), 3.71 (s, 3H), 5.30 (d, 1H, J=10.8 Hz), 5.61 (d, 1H, J=17.2 Hz), 5.98 (d, 1H, 10.4 Hz), 6.26 (dd, 1H, J=10.4, 17.2 Hz)

Reference Production Example 4

Methyl=(1R)-trans-3-[(1Z)-2-cyano-1,3-butadienyl]-2,2-dimethylcyclopropane carboxylate (483 mg, 2.36 mmol) was dissolved in a mixed liquid of 3 mL of tetrahydrofuran and 1 mL of water, and then potassium hydroxide (215 mg, 3.84 mmol) was added and the solution was stirred at room temperature for 24 hours. The reaction solution was added to 20 mL of ice water, and the solution was extracted with 20 mL of ethyl acetate. To the obtained aqueous layer, 5% hydrochloric acid was added until the pH became 2, and then the solution was extracted with 30 mL of ethyl acetate. The ethyl acetate layer washed twice with 20 mL of saturated brine and then dried over magnesium sulfate. After concentration under reduced pressure condition, 440 mg of (1R)-trans-3-[(1Z)-2-cyano-1,3-butadienyl]-2,2-dimethylcyclopropanecarboxylic acid represented by following formula:

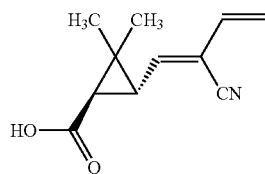

was obtained.

Colorless liquid: $^1$H-NMR (CDCl$_3$, TMS) δ (ppm): 1.25 (s, 3H), 1.38 (s, 3H), 1.82 (d, 1H, J=5.2 Hz), 2.56 (dd, 1H, J=10.4, 5.2 Hz), 5.32 (d, 1H, J=10.8 Hz), 5.62 (d, 1H, J=17.2 Hz), 6.01 (d, 1H, 10.4 Hz), 6.25 (dd, 1H, J=10.4, 17.2 Hz)

Reference Production Example 5

(1R)-trans-3-[(1Z)-2-cyano-1,3-butadienyl]-2,2-dimethylcyclopropanecarboxylic acid (440 mg, 2.30 mmol) was dissolved in 3 mL of tetrahydrofuran and then thionyl chloride (301 mg, 2.53 mmol) and 10 mg of N,N-dimethylformamide were added and the solution was stirred at room temperature for 1 hours, and further at 60° C. of 3 hours. The reaction solution was concentrated under reduced pressure condition to obtain 460 mg of (1R)-trans-3-[(1Z)-2-cyano-1,3-butadienyl]-2,2-dimethylcyclopropanecarboxylic acid chloride represented by the following formula:

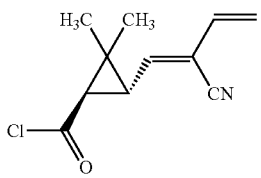

as a pale yellow liquid.

Formulation Examples are shown below. Parts are by mass.

Formulation Example 1

Twenty (20) parts any one of the present invention compounds (1) to (2) is dissolved in 65 parts of xylene and 15 parts of SOLPOL 3005X (a registered trademark of TOHO Chemical Industry Co., Ltd.) is added thereto and thoroughly mixed with stirring to obtain emulsifiable concentrates.

Formulation Example 2

Five (5) parts of SORPOL 3005X is added to 40 parts of any one of the present invention compounds (1) to (2) and the mixture is thoroughly mixed, and 32 parts of CARPLEX #80 (synthetic hydrated silicon oxide, a registered trademark of SHIONOGI & CO., LTD.) and 23 parts of 300-mesh diatomaceous earth are added thereto, followed by mixing with stirring by a mixer to obtain wettable powders.

Formulation Example 3

A mixture of 1.5 parts of any one of the present invention compounds (1) to (2), 1 part of TOKUSIL GUN (synthetic hydrated silicon oxide, manufactured by Tokuyama Corporation), 2 parts of REAX 85A (sodium lignin sulfonate, manufactured by West Vaco Chemicals), 30 parts of BENTONITE FUJI (bentonite, manufactured by Houjun) and 65.5 parts of SHOUKOUZAN A clay (kaoline clay, manufactured by Shoukouzan Kougyousho) is thoroughly pulverized and mixed, and water is added thereto. The mixture is thoroughly kneaded, granulated by an extruding granulator, and then dried to obtain 1.5% granules.

Formulation Example 4

To a mixture of 10 parts of any one of the present invention compounds (1) to (2), 10 parts of phenylxylylethane and 0.5 part of SUMIDUR L-75 (tolylene diisocyanate, manufactured by Sumitomo Bayer Urethane Co., Ltd.) is added 20 parts of 1.0% aqueous solution of gum arabic, and the mixture is stirred with a homomixer to obtain an emulsion having an average particle diameter of 20 μm. To the emulsion, 2 parts of ethylene glycol is added and the mixture is further stirred in a warm bath at a temperature of 60° C. for 24 hours to obtain microcapsule slurry. On the other hand, 0.2 part of xanthan gum and 1.0 part of VEEGUM R (aluminum magnesium silicate, manufactured by Sanyo Chemical Industries, Ltd.)

are dispersed in 56.3 parts of ion-exchanged water to obtain a thickener solution. Then, 42.5 parts of the above-mentioned microcapsule slurry and 57.5 parts of the above-mentioned thickener solution are mixed to obtain microcapsules.

Formulation Example 5

A mixture of 10 parts of any one of the present invention compounds (1) to (2) and 10 parts of phenylxylylethane is added to 20 parts of a 10% aqueous solution of polyethylene glycol, and the mixture is stirred by a homomixer to obtain an emulsion having an average particle diameter of 3 μm. On the other hand, 0.2 part of xanthan gum and 1.0 part of VEEGUM R (aluminum magnesium silicate, manufactured by Sanyo Chemical Industries, Ltd.) are dispersed in 58.8 parts of ion-exchanged water to obtain a thickener solution. Then, 40 parts of the above-mentioned emulsion solution and 60 parts of the above-mentioned thickener solution are mixed to obtain flowable formulations.

Formulation Example 6

To 5 parts of any one of the present invention compounds (1) to (2), 3 parts of CARPLEX #80 (synthetic hydrated silicon oxide, a registered trademark of SHIONOGI & CO., LTD.), 0.3 part of PAP (a mixture of monoisopropyl phosphate and diisopropyl phosphate) and 91.7 parts of talc (300 mesh) are added and the mixture is stirred by a mixer to obtain dusts.

Formulation Example 7

Zero point one (0.1) part of any one of the present invention compounds (1) to (2) is dissolved in 10 parts of dichloromethane and the solution is mixed with 89.9 parts of deodorized kerosine to obtain oil solutions.

Formulation Example 8

Zero point one (0.1) part of each of any one of the present invention compounds (1) to (2) and 39.9 parts of deodorized kerosine are mixed and dissolved, and the solution is filled into an aerosol container and a valve portion is installed. Then, 60 parts of power propellant (liquefied petroleum gas) is filled therein under pressure through the valve portion to obtain oil-based aerosol formulations.

Formulation Example 9

Zero point six (0.6) part of any one of the present invention compounds (1) to (2), 5 parts of xylene, 3.4 parts of deodorized kerosine and 1 part of Reodol MO-60 (emulsifier, a registered trademark of Kao Corporation) are mixed and dissolved, and the solution and 50 parts of water are filled into an aerosol container, and then 40 parts of power propellant (liquefied petroleum gas) is filled therein under pressure through a valve portion to obtain aqueous aerosol formulations.

Formulation Example 10

Zero point three (0.3) g of any one of the present invention compounds (1) to (2) is dissolved in 20 ml of acetone and the solution is uniformly mixed with stirring with 99.7 g of a base material for a coil (obtained by mixing Tabu powder, Pyrethrum marc and wooden powder at a ratio of 4:3:3). Then, 100 ml of water is added thereto, and the mixture is thoroughly kneaded, dried and molded to obtain insecticidal coils.

Formulation Example 11

A mixture of 0.8 g of any one of the present invention compounds (1) to (2) and 0.4 g of piperonyl butoxide is dissolved in acetone and the total volume is adjusted to 10 ml. Then, 0.5 ml of this solution is uniformly impregnated into a base material for an insecticidal mat for electric heating (a plate obtained by hardening fibrils of a mixture of cotton linters and pulp) having a size of 2.5 cm×1.5 cm and a thickness of 0.3 cm to obtain insecticidal mats for electric heating.

Formulation Example 12

A solution obtained by dissolving 3 parts of any one of the present invention compounds (1) to (2) in 97 parts of deodorized kerosine is poured into a vessel made of vinyl chloride. A liquid absorptive core whose upper part can be heated by a heater (an inorganic pulverized powder is hardened with a binder and sintered) is inserted thereinto to obtain parts to be used for a liquid absorptive core type thermal transpiring apparatus.

Formulation Example 13

One hundred (100) mg of any one of the present invention compounds (1) to (2) is dissolved in an appropriate amount of acetone and the solution is impregnated into a porous ceramic plate having a size of 4.0 cm×4.0 cm and a thickness of 1.2 cm to obtain thermal fumigants.

Formulation Example 14

One hundred (100) μg of any one of the present invention compounds (1) to (2) is dissolved in an appropriate amount of acetone and the solution is uniformly applied to filter paper having a size of 2 cm×2 cm and a thickness of 0.3 mm, and air-dried to remove acetone, and thus volatile agents for using at room temperature are obtained.

Formulation Example 15

Ten (10) parts of any one of the present invention compounds (1) to (2), 35 parts of white carbon containing 50 parts of a polyoxyethylene alkyl ether sulfate ammonium salt, and 55 parts of water are mixed and then finely ground by a wet grinding method to obtain 10% formulations.

Next, it will be demonstrated by Test Examples that the compound of the present invention is effective as an active ingredient of a pest controlling agent.

Test Example 1

Each of the present invention compounds (1) and (2) (0.00625 parts) produced in the aforementioned Production Examples was dissolved in 10 parts of dichloromethane and the resulting solution was mixed with 89.99375 parts of an isoparafin solvent (Isper M, registered trademark of Exxon Chemical Company) to prepare a 0.00625% (w/v) oil solution.

Ten houseflies (5 of each male and female) were released in a cubic chamber having a side length of 70 cm and then 0.7 ml of the present invention compound (1) was sprayed through a small window at an inlet of the chamber using a spray gun (spray pressure: 0.9 kg/cm$^2$). The number of knockdowned houseflies was counted after a given time had passed since completion of spraying, and a knockdown rate (KD rate) was determined (repeated twice). The test was carried out in the same manner, except that the present invention compound (2) was used in place of the present invention compound (1), and then a knockdown rate was determined after a given time (repeated twice).

The results are shown in Table 1.

TABLE 1

| Test compound | Knockdown rate (%) after 7 minutes |
|---|---|
| Present invention Compound (1) | 100 |
| Present invention compound (2) | 100 |

Industrial Applicability

The compound of the present invention has an excellent pest control effect and is therefore useful as an active ingredient of a pest control agent.

The invention claimed is:

1. An ester compound represented by formula (1):

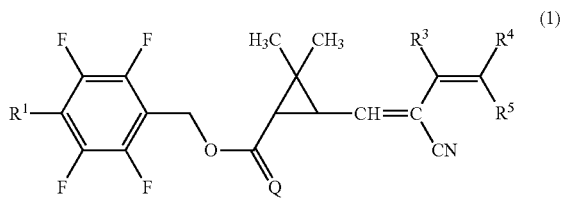

wherein $R^1$ represents hydrogen, fluorine, C1-C4 alkyl, C1-C4 alkoxy, C1-C4 alkoxymethyl, or C1-C4 alkylthiomethyl; $R^3$ represents hydrogen or methyl, $R^4$ represents hydrogen or C1-C4 alkyl, and $R^5$ represents hydrogen or C1-C4 alkyl.

2. The ester compound according to claim 1, wherein the relative configuration of the substituent at the 1-position of the cyclopropane ring and the substituent at the 3-position of the cyclopropane ring is a trans configuration in formula (1).

3. The ester compound according to claim 1, wherein the absolute configuration of the 1-position of the cyclopropane ring is an R configuration in formula (1).

4. The ester compound according to claim 1, wherein the absolute configuration of the 1-position of the cyclopropane ring is an R configuration, and the relative configuration of the substituent at the 1-position of the cyclopropane ring and the substituent at the 3-position of the cyclopropane ring is a trans configuration in formula (1).

5. The ester compound according to claim 1, wherein the relative configuration of the substituent at the 1'-position is Z-configuration in formula (1).

6. The ester compound according to claim 1, wherein the absolute configuration of the 1-position of the cyclopropane ring is an R configuration and the relative configuration of the substituent of the 1'-position is Z-configuration in formula (1).

7. The ester compound according to claim 1, wherein the absolute configuration of the 1-position of the cyclopropane ring is an R configuration, the relative configuration of the substituent at the 1-position of the cyclopropane ring and the substituent at the 3-position of the cyclopropane ring is a trans configuration, and the relative configuration of the substituent of the 1'-position is Z-configuration in formula (1).

8. The ester compound according to claim 1, wherein $R^3$ is hydrogen in formula (1).

9. The ester compound according to claim 1, wherein $R^4$ is hydrogen or methyl in formula (1).

10. The ester compound according to claim 1, wherein $R^4$ is hydrogen in formula (1).

11. The ester compound according to claim 1, wherein $R^4$ is methyl in formula (1).

12. The ester compound according to claim 1, wherein $R^5$ is hydrogen in formula (1).

13. The ester compound according to claim 1, wherein $R^3$ is hydrogen and $R^4$ is hydrogen or methyl in formula (1).

14. The ester compound according to claim 1, wherein $R^3$ is hydrogen and $R^4$ is hydrogen in formula (1).

15. The ester compound according to claim 1, wherein $R^3$ is hydrogen and $R^4$ is methyl in formula (1).

16. The ester compound according to claim 1, wherein $R^3$ is hydrogen and $R^5$ is hydrogen in formula (1).

17. The ester compound according to claim 1, wherein $R^4$ is hydrogen or methyl, and $R^5$ is hydrogen in formula (1).

18. The ester compound according to claim 1, wherein $R^4$ is hydrogen and $R^5$ is hydrogen in formula (1).

19. The ester compound according to claim 1, wherein $R^4$ is methyl and $R^5$ is hydrogen in formula (1).

20. The ester compound according to, claim 1, wherein $R^3$ is hydrogen, $R^4$ is hydrogen or methyl, and $R^5$ is hydrogen in formula (1).

21. The ester compound according to claim 1, wherein $R^3$ is hydrogen, $R^4$ is hydrogen, and $R^5$ is hydrogen in formula (1).

22. The ester compound according to claim 1, wherein $R^3$ is hydrogen, $R^4$ is methyl, and $R^5$ is hydrogen in formula (1).

23. The ester compound according to claim 1, wherein $R^1$ is methoxymethyl in formula (1).

24. A pest control agent comprising the ester compound according to claim 1 and an inert carrier.

25. A method of controlling pests, which comprises a step of applying an effective amount of the ester compound according to claim 1 to pests or a place where pests inhabit.

26. A method of controlling pests, wherein said pests are cockroaches, which comprises the step of applying an effective amount of the ester compound according to claim 1 to cockroaches or a place where cockroaches inhabit.

27. The method of controlling pests according to claim 26, wherein the cockroach is American cockroach (*Periplaneta Americana*).

28. The method of controlling pests according to claim 26, wherein the cockroach is German cockroach (*Blattella germanica*).

29. A method of controlling pests, wherein said pests are cockroaches, which comprises a step of spraying an effective amount of the ester compound according to claim 1 to cockroaches or a place where cockroaches inhabit.

30. The method of controlling pests according to claim 29, wherein the cockroach is American cockroach (*Periplaneta Americana*).

31. The method of controlling pests according to claim 29, wherein the cockroach is German cockroach (*Blattella germanica*).

* * * * *